(12) United States Patent
Totaro et al.

(10) Patent No.: US 12,378,267 B2
(45) Date of Patent: Aug. 5, 2025

(54) SYNTHESIS OF FMOC-PROTECTED MORPHOLINO MONOMERS AND OLIGOMERS

(71) Applicant: Entrada Therapeutics, Inc., Boston, MA (US)

(72) Inventors: Kyle A. Totaro, Attleboro, MA (US); Ziqing Qian, Wellesley, MA (US)

(73) Assignee: Entrada Therapeutics, Inc., Boston, MA (US)

( * ) Notice: Subject to any disclaimer, the term of this patent is extended or adjusted under 35 U.S.C. 154(b) by 0 days.

(21) Appl. No.: 17/806,395

(22) Filed: Jun. 10, 2022

(65) Prior Publication Data

US 2023/0097585 A1    Mar. 30, 2023

Related U.S. Application Data

(60) Provisional application No. 63/211,881, filed on Jun. 17, 2021.

(51) Int. Cl.
*C07D 473/30* (2006.01)
*C07F 9/6561* (2006.01)

(52) U.S. Cl.
CPC ................................ *C07F 9/65616* (2013.01)

(58) Field of Classification Search
CPC .................................................. C07D 473/30
See application file for complete search history.

(56) References Cited

U.S. PATENT DOCUMENTS

| | | |
|---|---|---|
| 5,034,506 A | 7/1991 | Summerton et al. |
| 5,142,047 A | 8/1992 | Summerton et al. |
| 5,166,315 A | 11/1992 | Summerton et al. |
| 5,185,444 A | 2/1993 | Summerton et al. |
| 5,217,866 A | 6/1993 | Summerton et al. |
| 5,235,033 A | 8/1993 | Summerton et al. |
| 5,506,337 A | 4/1996 | Summerton et al. |
| 5,521,063 A | 5/1996 | Summerton et al. |
| 5,698,685 A | 12/1997 | Summerton et al. |
| 5,859,233 A | 1/1999 | Hirschbein et al. |
| 6,828,105 B2 | 12/2004 | Stein et al. |
| 7,850,949 B2 | 12/2010 | Fang |
| 7,943,762 B2 | 5/2011 | Weller et al. |
| 8,067,571 B2 | 11/2011 | Weller et al. |
| 8,076,476 B2 | 12/2011 | Reeves et al. |
| 8,299,206 B2 | 10/2012 | Fox et al. |
| 8,969,551 B2 | 3/2015 | Ueda |
| 9,161,948 B2 | 10/2015 | Hanson |
| 9,610,362 B2 | 4/2017 | Armstrong |
| 10,077,443 B2 | 9/2018 | Albaek et al. |
| 10,415,036 B2 | 9/2019 | Torii et al. |
| 12,012,427 B2 * | 6/2024 | Sinha ................... C08G 73/06 |
| 2005/0261249 A1 | 11/2005 | Iversen et al. |
| 2006/0276425 A1 | 12/2006 | Mourich et al. |
| 2007/0004661 A1 | 1/2007 | Stein et al. |
| 2007/0129323 A1 | 6/2007 | Stein et al. |
| 2009/0131624 A1 * | 5/2009 | Reeves ................... C08G 73/06 544/118 |
| 2010/0016215 A1 | 1/2010 | Moulton et al. |
| 2010/0130591 A1 | 5/2010 | Sazani et al. |
| 2010/0234281 A1 | 9/2010 | Weller et al. |
| 2011/0269665 A1 | 11/2011 | Kole |
| 2014/0303238 A1 | 10/2014 | Linsley et al. |
| 2014/0329772 A1 | 11/2014 | Linsley et al. |
| 2019/0292208 A1 | 9/2019 | Cai et al. |
| 2019/0365918 A1 | 12/2019 | Bestwick et al. |
| 2020/0377886 A1 | 12/2020 | Passini et al. |
| 2021/0130379 A1 | 5/2021 | Sinha et al. |

FOREIGN PATENT DOCUMENTS

| | | |
|---|---|---|
| WO | WO-02092617 A1 | 11/2002 |
| WO | WO-2009005793 A2 | 1/2009 |
| WO | WO-2019060862 A1 | 3/2019 |
| WO | WO-2019165183 A1 | 8/2019 |
| WO | WO-2022125984 A1 | 6/2022 |
| WO | WO-2022125987 A1 | 6/2022 |
| WO | WO-2022240758 A1 | 11/2022 |
| WO | WO-2022240760 A2 | 11/2022 |
| WO | WO-2023081893 A1 | 5/2023 |

OTHER PUBLICATIONS

American Chemical Society. Chemical Abstract Service. RN 2478484-06-7. Entered into STN: Sep. 11, 2020. (Year: 2020).*
Abramova, Tatyana V., et al., "Solid-phase-supported synthesis of morpholinoglycine oligonucleotide mimics", Beilstein J. Org. Chem. 10, (2014), 1151-1158.
Bhadra, Jhuma, et al., "Corrigendum to "Synthesis of phosphorodiamidate morpholino oligonucleotides by H-phosphonate method" [Tetrahedron Lett. 56 (2015) 4565-4568]", Tetrahedron Letters 59, (2018), 1974-1975.
Bhadra, Jhuma, et al., "Synthesis of Morpholino Monomers, Chlorophosphoramidate Monomers, and Solid-Phase Synthesis of Short Morpholino Oligomers", Curr. Protoc. Nucleic Acid Chem. 62:4.65.1-4.65.26., (Sep. 2015), 26 pgs.
Bhadra, Jhuma, et al., "Synthesis of phosphorodiamidate morpholino oligonucleotides by H-phosphonate method", Tetrahedron Letters 56, (2015), 4565-4568.
Inagaki, Masahito, et al., "N-Benzoyl-protected Peptide Nucleic Acid (PNA) Monomers Expand the Range of Nucleobases Available for PNA-DNA Chimera", Chem. Lett., 48, The Chemical Society of Japan, (2019), 341-344.
Kundu, Jayanta, et al., "Synthesis of Phosphorodiamidate Morpholino Oligonucleotides Using Trityl and Fmoc Chemistry in an Automated Oligo Synthesizer", J. Org. Chem., 87, (2022), 9466-9478.
Li, Chenxi, et al., "Fully automated fast-flow synthesis of antisense phosphorodiamidate morpholino oligomers", Nature Communications, 12:4396, (2021), 8 pgs.

(Continued)

*Primary Examiner* — John S Kenyon
(74) *Attorney, Agent, or Firm* — Mueting Raasch Group

(57) ABSTRACT

The present disclosure provides the synthesis of phosphorodiamidate morpholino oligomers (PMOs) in high purity, yield, and efficiency from Fmoc-protected morpholino monomers, e.g., Fmoc morpholino monomer G.

20 Claims, 18 Drawing Sheets

Specification includes a Sequence Listing.

(56) References Cited

OTHER PUBLICATIONS

Summerton, James, et al., "Morpholino Antisense Oligomers: Design, Preparation, and Properties", Antisense & Nucleic Acid Drug Develoopment 7, (1997), 187-195.
Summerton, James E, "Morpholinos and PNAs compared", Letters in Peptide Science, 10, Kluwer, (2003), 215-236.
Arthanari, Y, et al., "Delivery of therapeutic shRNA and siRNA by Tat fusion peptide targeting bcr-abl fusion gene in Chronic Myeloid Leukemia cells", J. Controlled Release 145, (2010), 272-280.
Clayton, N. P., et al., "Antisense Oligonucleotide-Mediated Suppression of Muscle Glycogen Synthase 1 Synthesis as an Approach for Substrate Reduction Therapy of Pompe Disease", Molecular Therapy-Nucleic Acids 3, e206, (2014), 11 pgs.
Dastpeyman, M, et al., "Endosomal escape cell-penetrating peptides significantly enhance pharmacological effectiveness and CNS activity of systemically administered antisense oligonucleotides", International Journal of Pharmaceutics 599, p. 120398, (2021), 10 pgs.
Dowdy, Steven F, "Overcoming cellular barriers for RNA therapeutics", Nat. Biotechnol. 35(3), (Mar. 2017), 222-229.
Dyne Therapeutics, "Building the World's Leading Muscle Disease Company", Company Overview, 39th Annual J.P. Morgan Healthcare Conference, (Jan. 13, 2021), 31 pgs.
Fadzen, et al., "Chimeras of Cell-Penetrating Peptides Demonstrate Synergistic Improvement in Antisense Efficacy", Biochemistry, vol. 58, Iss. 38, (Aug. 1, 2019), 30 pgs.
Jirka, M. G Silvana, et al., "Cyclic Peptides to Improve Delivery and Exon Skipping of Antisense Oligonucleotides in a Mouse Model for Duchenne Muscular Dystrophy", Molecular Therapy, US, vol. 26, No. 1, (Jan. 2018), 16 pgs.
Khvorova, Anastasia, "The chemical evolution of oligonucleotide therapies of clinical utility", Nat Biotechnol., 35(3), (Mar. 2017), 238-248.
Kreher, Nerissa C, et al., "A Novel EEV-Conjugated PMO, ENTR-701, Reduces Nuclear Foci and Corrects Aberrant Splicing in Myotonic Dystrophy Type 1 Preclinical Models", 2022 Myotonic Dystrophy Foundation Annual Conference, New Directions in Biology and Disease of Skeletal Muscle, (2022), 2 pgs.
Leger, A. J., et al., "Systemic Delivery of a Peptide-Linked Morpholino Oligonucleotide Neutralizes Mutant RNA Toxicity in a Mouse Model of Myotonic Dystrophy", Nucleic Acid Therapeutics, United States, vol. 2, No. 2, (Apr. 4, 2013), 109-117.
Lim, K. R. Q., et al., "DUX4 Transcript Knockdown with Antisense 2'-O-Methoxyethyl Gapmers for the Treatment of Facioscapulohumeral Muscular Dystrophy", Molecular Therapy, vol. 29, No. 2, (Feb. 2021), 548-558.
Lim, K. R. Q., et al., "Inhibition of DUX4 expression with antisense LNA gapmers as a therapy for facioscapulohumeral muscular dystrophy", PNAS, vol. 117, No. 35, p. 21823 (Correction pg), (Sep. 1, 2020), 1 pg.
Lim, K. R. Q., et al., "Inhibition of DUX4 Expression With Antisense LNA Gapmers as a Therapy for Facioscapulohumeral Muscular Dystrophy", PNAS, vol. 117, No. 28, (Jul. 14, 2020), 16509-16515.
Lu-Nguyen, Ngoc, et al., "Systemic antisense therapeutics inhibiting DUX4 expression improves muscle function in an FSHD mouse model", BIORXIV DOI: 10.1101/2021.01.14.426659, XP055944678, (Jan. 16, 2021), 40 pgs.
Marsollier, A, et al., "Antisense Targeting Of 3' End Elements Involved In DUX4 mRNA Processing Is An Efficient Therapeutic Strategy For Facioscapulohumeral Dystrophy: A New Gene-silencing Approach", Human molecular genetics, 25(8), (2016), 1468-1478.
Pritz, S, et al., "Synthesis of Biologically Active Peptide Nucleic Acid-Peptide Conjugates by Sortase-Mediated Ligation", Journal of Organic Chemistry 72(10), (2007), 3909-3912.
Sajid, M. I., et al., "Applications of Amphipathic And Cationic Cyclic Cell-penetrating Peptides: Significant Therapeutic Delivery Tool", Peptides, Elsevier, Amsterdam, NL, vol. 141, 170542, (Mar. 29, 2021), 15 pgs.
Wolfe, M. Justin, et al., "Perfluoroaryl Bicyclic Cell-Penetrating Peptides for Delivery of Antisense Oligonucleotides", Angewandte Chemie, Wiley-VCH Verlag GMBH & CO. KGAA, DE, vol. 130, No. 17, (Feb. 25, 2018), 4846-4849.
Yin, Hao, et al., "Non-viral vectors for gene-based therapy", Nature Reviews Genetics, vol. 15, (Aug. 2014), 541-555.
Bi Y., et al., "siRNA Delivery Using Lipid Nanoparticle Modified with Cell Penetrating Peptide," Nanomedicine: Nanotechnology, Biology, and Medicine, Jul. 17, 2018, vol. 14, No. 5, p. 1878, DOI:10.1016/J.NANO.2017.11.365, Issn 1549-9634, XP085426707.
Blenke E.O., "Intracellular Delivery Of RNA Therapeutics With Lipid Nanoparticles," Thesis, Utrecht University, Jan. 25, 2017, 164 Pages, XP055556387, [Retrieved on Feb. 13, 2019] Retrieved from URL: https://dspace.library.uu.nl/bitstream/handle/1874/343775/Oude_Blenke.pdf?sequence=1&isAll owed=y.
Claeboe C.D., et al., "3'-Modified Oligonucleotides by Reverse DNA Synthesis," Nucleic Acids Research, Oct. 1, 2003, vol. 31, No. 19, pp. 5685-5691, XP055423008.
Hölz K., et al., "High-Efficiency Reverse (5'→3') Synthesis of Complex DNA Microarrays," Scientific Reports, Oct. 10, 2018, vol. 8, No. 1, pp. 1-12, XP055685061.
International Search Report and Written Opinion for International Application No. PCT/US2023/070154, mailed Mar. 26, 2024, 37 Pages.
Kanatsu, K et al. "Discovery and characterization of stereodefined PMO gapmers targeting tau," 2024 bioRxiv May 9, 2024; doi: 10.1101/2024.05.09.591947. preprint.
Langner H.K., et al., "Synthesis and Characterization of Thiophosphoramidate Morpholino Oligonucleotides and Chimeras," Journal of the American Chemical Society, Aug. 31, 2020, vol. 142, No. 38, p. 16240-16253, XP055802911, Retrieved from the Internet: URL: https://pubs.acs.org/doi/10.1021/jacs.0c04335.
Paul S., et al., "Synthesis of Phosphorodiamidate Morpholino Oligonucleotides and Their Chimeras Using Phosphoramidite Chemistry," Journal of the American Chemical Society, Dec. 7, 2016, vol. 138, No. 48, p. 15663-15672, XP055389989.

* cited by examiner

Compound ID: Fmoc Morpholino G Monomer

Compound ID: Fmoc Morpholino G Monomer

SEQUENCE LISTING

<160> NUMBER OF SEQ ID NOS: 1

<210> SEQ ID NO 1
<211> LENGTH: 12
<212> TYPE: DNA
<213> ORGANISM: Artificial Sequence
<220> FEATURE:
<223> OTHER INFORMATION: A synthetic sequence

<400> SEQUENCE: 1
tgaaaacgcc gc                                                          12

SYNTHESIS OF FMOC-PROTECTED MORPHOLINO MONOMERS AND OLIGOMERS

CROSS-REFERENCE TO RELATED APPLICATIONS

This application claims priority to U.S. provisional patent application No. 63/211,881, which was filed on Jun. 17, 2021, the disclosure of which is hereby incorporated by reference in its entirety.

BACKGROUND

Sequence Listing

This application contains a Sequence Listing electronically submitted to the United States Patent and Trademark Office via EFS-Web as an ASCII text file entitled "5892020US1_SL.TXT" having a size of 546 bytes and created on Jun. 10, 2022. Due to the electronic filing of the Sequence Listing, the electronically submitted Sequence Listing serves as both the paper copy required by 37 CFR § 1.821 (c) and the computer readable form (CRF) required by § 1.821 (e). The information contained in the Sequence Listing is incorporated by reference herein.

Phosphorodiamidate morpholino oligomers (PMOs) are nucleic acid analogs which bind complementary sequences in target mRNA, and thus are useful in modulating protein synthesis, and ultimately, gene expression. These oligomers are composed of base-pairing recognition moieties (heterocyclic bases) supported by a morpholino backbone system. While some morpholino subunits for use in synthesizing such oligomers can be prepared from readily available ribonucleosides, others are either more difficult to prepare or include protecting groups that complicate subsequent coupling steps. Accordingly, for at least these reasons, synthesis of PMOs is generally challenging and lengthy—factors that significantly limit their widespread application and clinical translation as antisense therapies for various diseases.

Therefore, improved methods are needed to increase yield, purity, and efficiency in PMO synthesis, particularly in the case of G morpholino subunits.

SUMMARY

In one aspect, the present disclosure provides a compound of Formula (I):

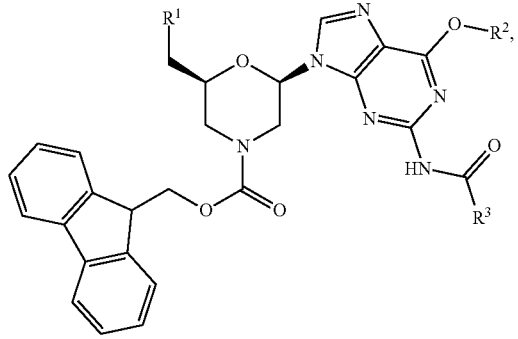

(I)

wherein:

$R^1$ is a protected or unprotected hydroxyl group, a chlorophosphoramidate group, a phosphoramidate linkage to the morpholino ring nitrogen of a morpholino subunit monomer, a phosphoramidate linkage to the morpholino ring nitrogen of a morpholino subunit in a morpholino oligomer, or a linkage to a solid support;

$R^2$ is H, alkyl or alkylenearyl, each of which is optionally substituted; and $R^3$ is alkyl, alkylenearyl (e.g., —CH$_2$Ph), or alkylenearyloxy (e.g., —CH$_2$OPh), each of which is optionally substituted, provided that when $R^2$ is H, $R^3$ is not —CH(CH$_3$)$_2$.

In another aspect, the present disclosure provides a method of preparing a phosphoramidate morpholino oligomer (PMO), comprising: coupling a morpholino subunit monomer or an oligomer thereof with a monomer of Formula (I) having the structure:

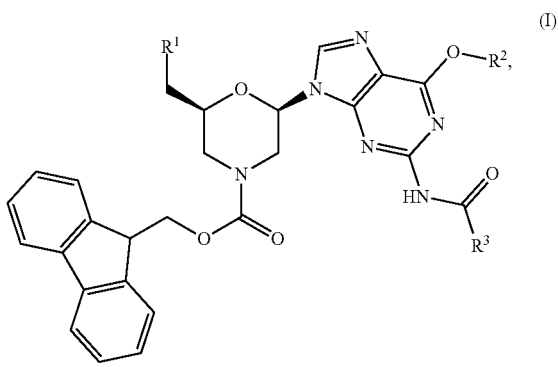

(I)

wherein:

$R^1$ is a protected or unprotected hydroxyl group, a chlorophosphoramidate group, a phosphoramidate linkage to the morpholino ring nitrogen of a morpholino subunit monomer, a phosphoramidate linkage to the morpholino ring nitrogen of a morpholino subunit in a morpholino oligomer, or a linkage to a solid support;

$R^2$ is H, alkyl or alkylenearyl, each of which is optionally substituted; and $R^3$ is alkyl, alkylenearyl (e.g., —CH$_2$Ph), or alkylenearyloxy (e.g., —CH$_2$OPh), each of which is optionally substituted, provided that when $R^2$ is H, $R^3$ is not —CH(CH$_3$)$_2$.

In embodiments, the PMO has the structure of Formula (V):

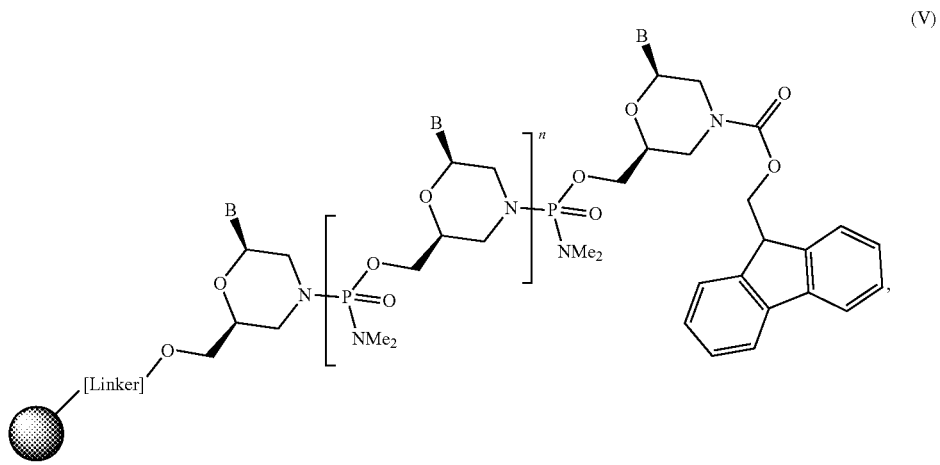

(V)

wherein:
B is a nucleobase selected from the group consisting of adenine, cytosine, guanine and thymine, wherein at least one B is guanine;
"Linker" is a functional handle covalently attaching a morpholino subunit monomer to a solid support, which comprises of either trityl (e.g., 2-chlorotrityl), aminomethyl, p-alkoxybenzyl alcohol, 4-(4-hydroxymethyl-3-methoxyphenoxy)butyric acid, 4-[(2,4-dimethoxyphenyl)(amino)methyl]phenoxyacetic acid, or (RS)-2-{[5-(Fmoc-amino)dibenzo[a,d]cycloheptane-2-yl]oxy}acetic acid, each of which is optionally functionalized with a succinic acid; and
n is 0 to 30.

In some embodiments, the PMO has the structure of Formula (VI):

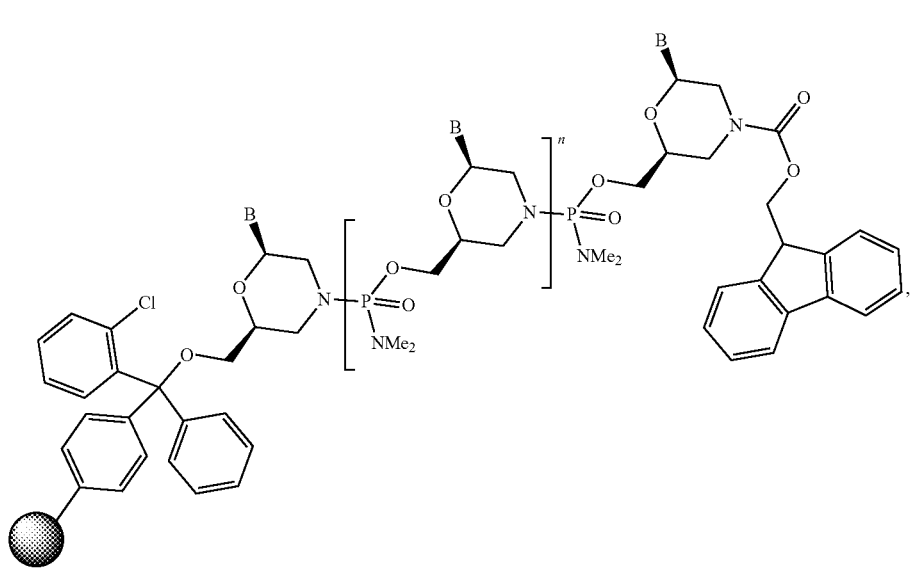

(VI)

wherein:
B is a nucleobase selected from adenine, cytosine, guanine and thymine, wherein at least one B is guanine; and
n is 0 to 30.

Figure 3A:
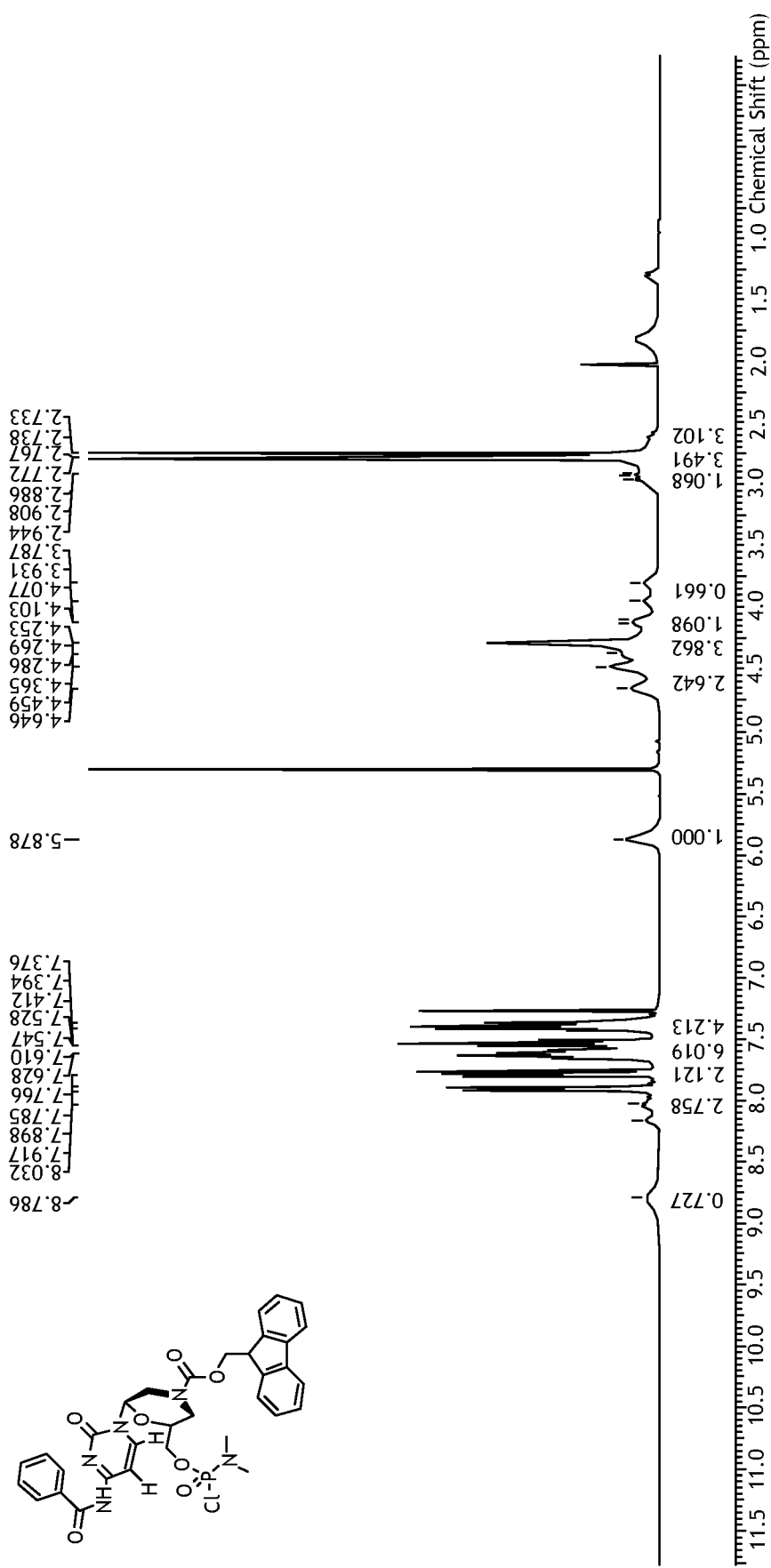

FIG. 3A shows the $^1$H NMR (400 MHz, CDCl3) of Fmoc Monomer C.

Figure 3B:
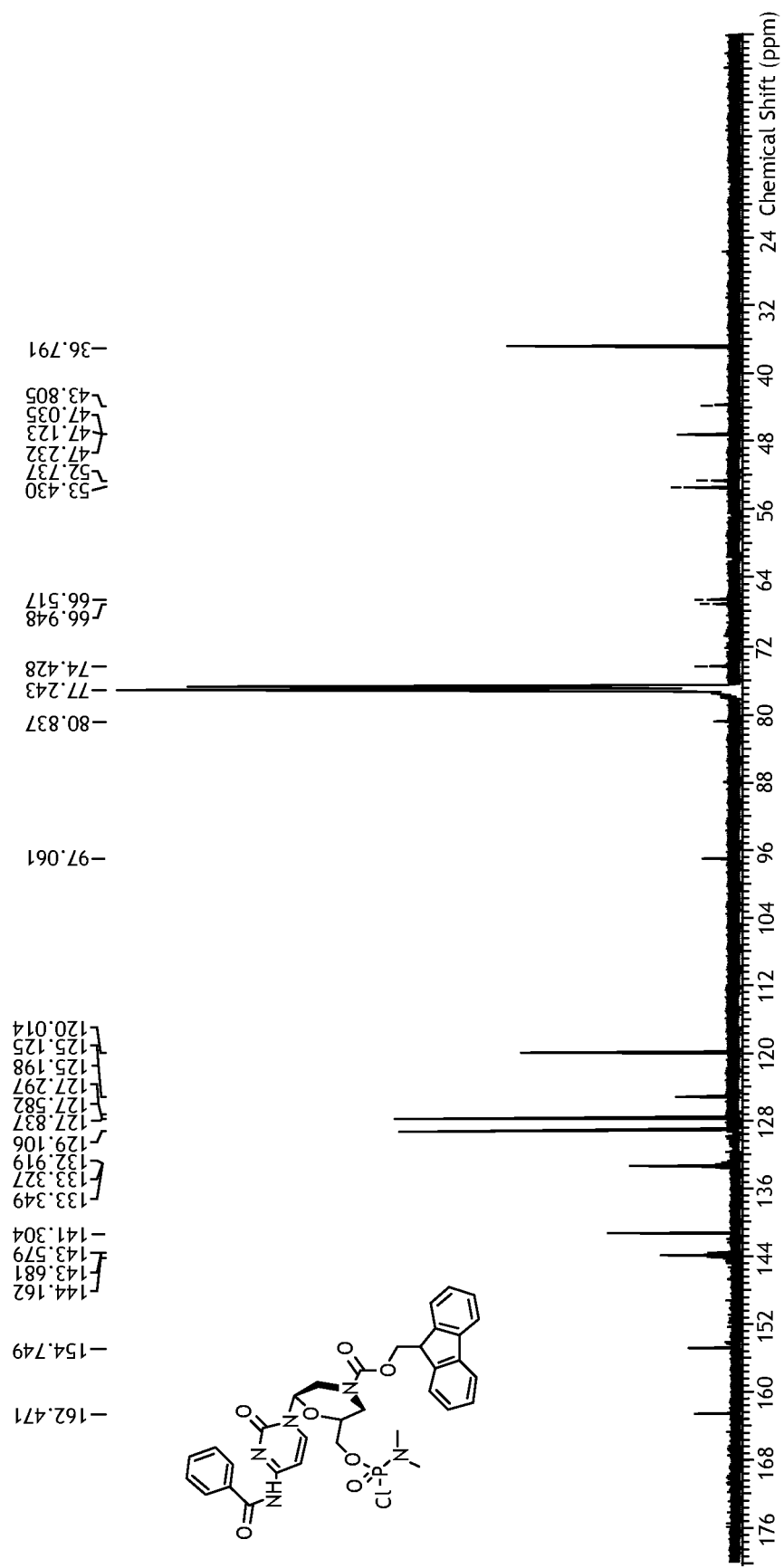

FIG. 3B shows the $^{13}$C NMR (CDCl3) of Fmoc Monomer C.

Figure 3C:
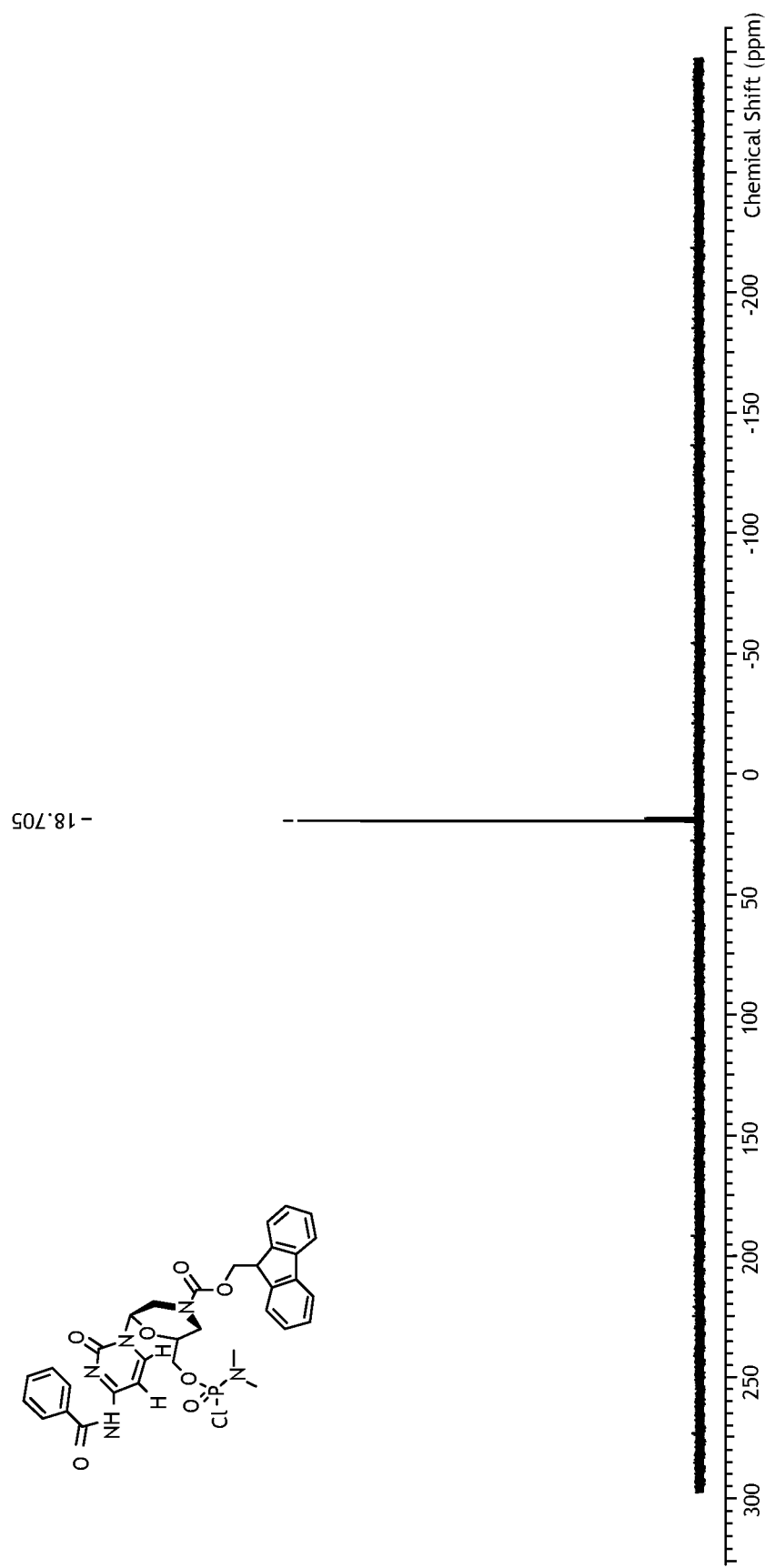

FIG. 3C shows the $^{31}$P NMR (CDCl3) of Fmoc Monomer C.

Figure 3D:
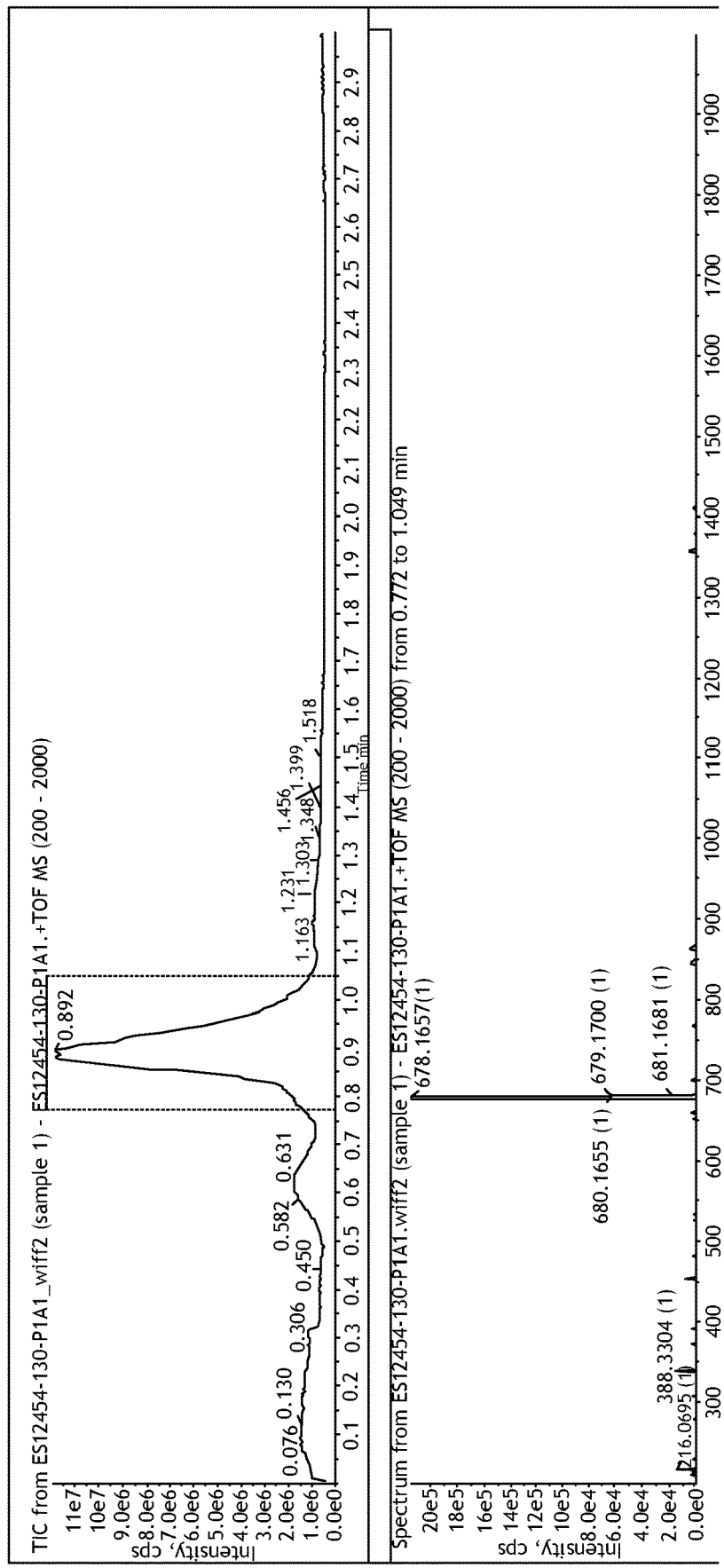

FIG. 3D shows the LCMS chromatogram of Fmoc Monomer C (calculated molecular weight=678.08).

Figure 4A:
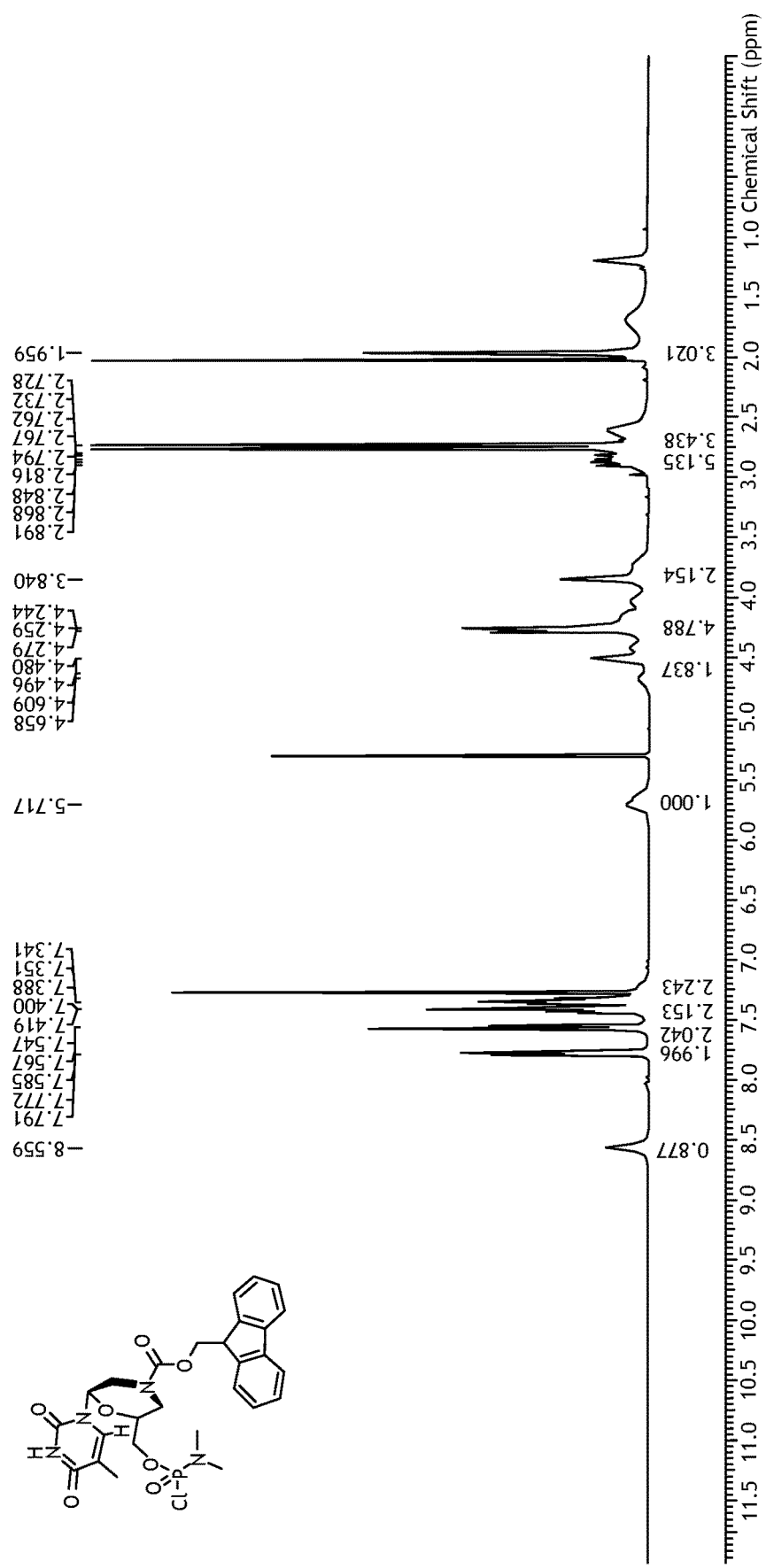

FIG. 4A shows the $^1$H NMR (400 MHz, CDCl3) of Fmoc Monomer T.

Figure 4B:
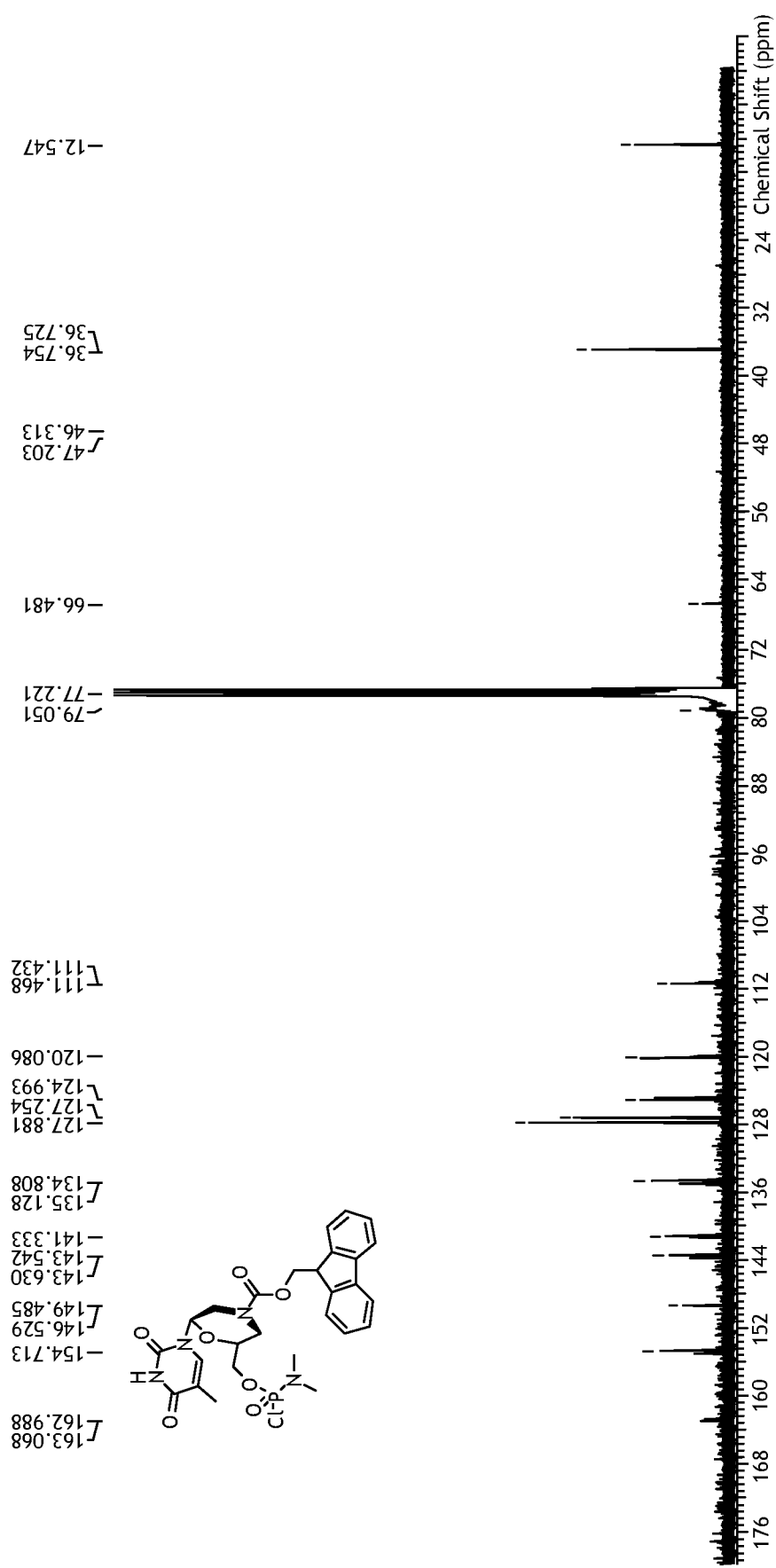

FIG. 4B shows the $^{13}$C NMR (CDCl3) of Fmoc Monomer T.

Figure 4C:
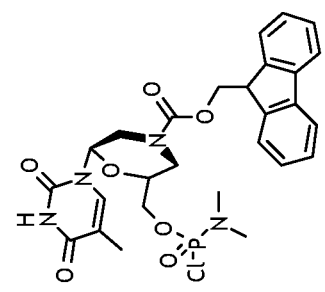
Figure 4C:
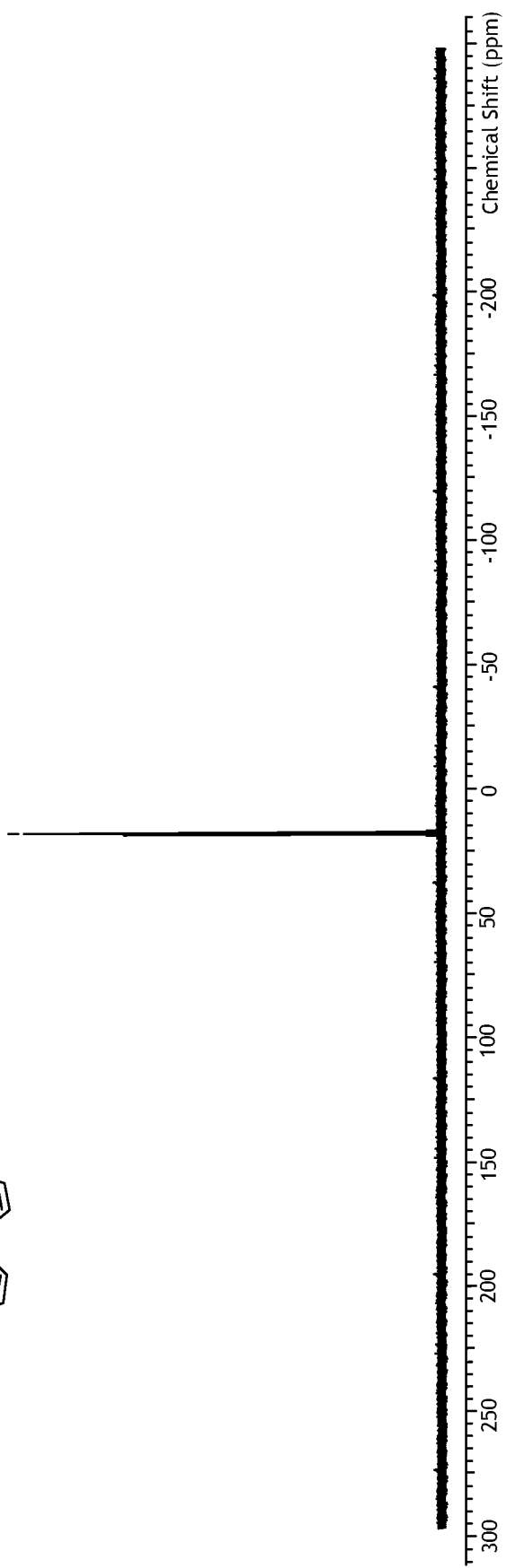

FIG. 4C shows the $^{31}$P NMR (CDCl3) of Fmoc Monomer T.

Figure 4D:
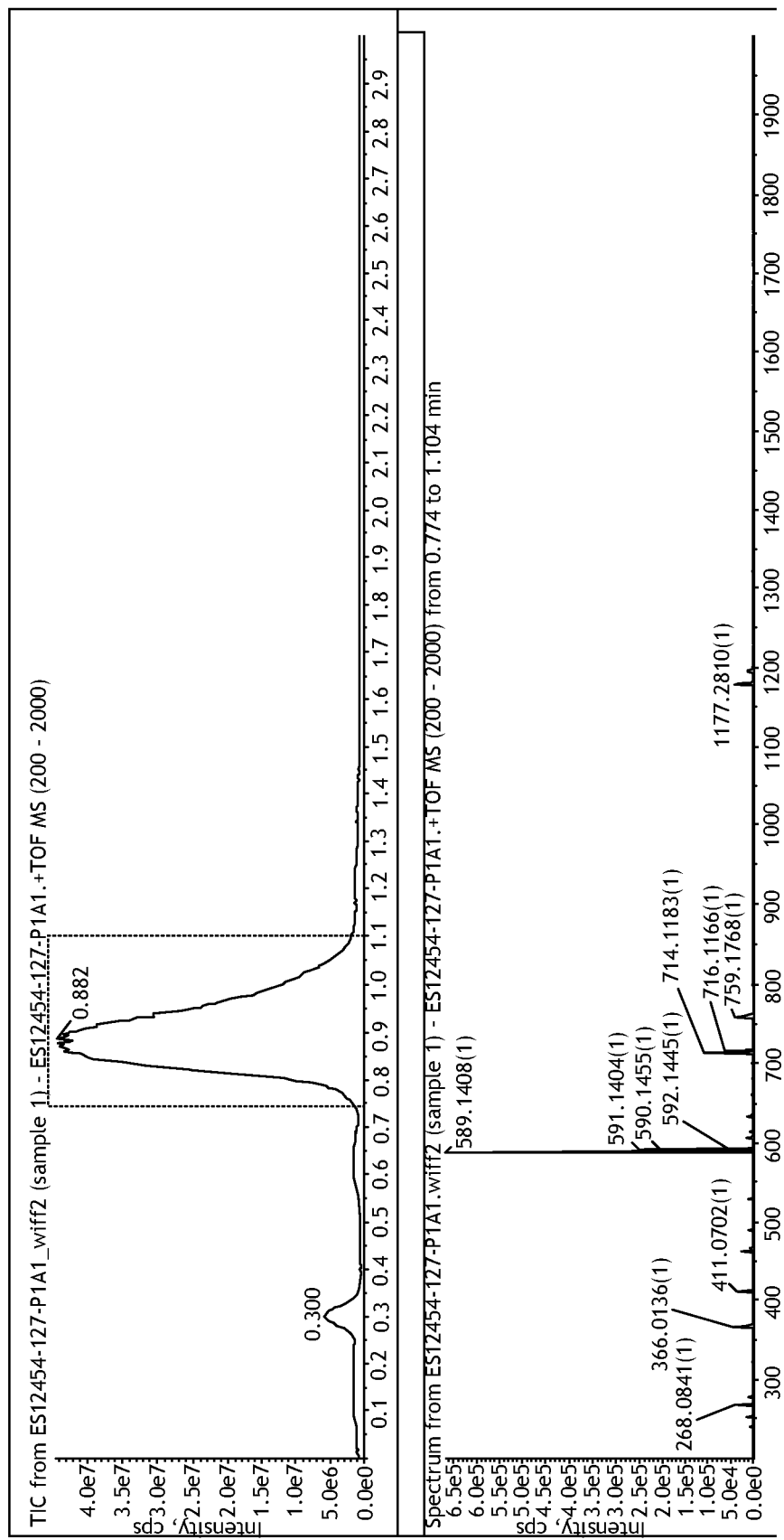

FIG. 4D shows the LCMS chromatogram of Fmoc Monomer T (calculated molecular weight=558.98).

Figure 5A:
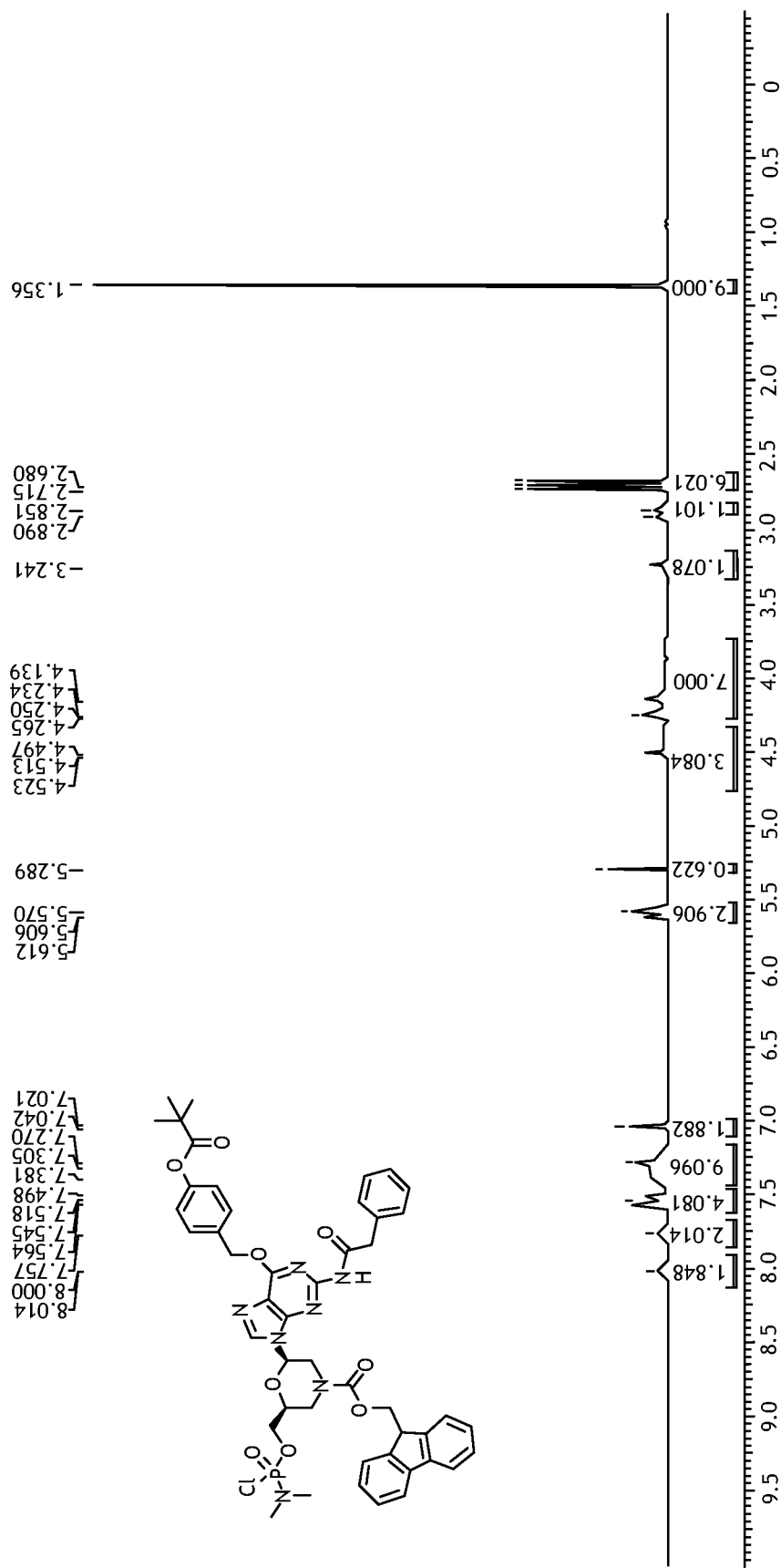

FIG. 5A shows the $^1$H NMR (400 MHz, CDCl3) of Fmoc Monomer G.

Figure 5B:
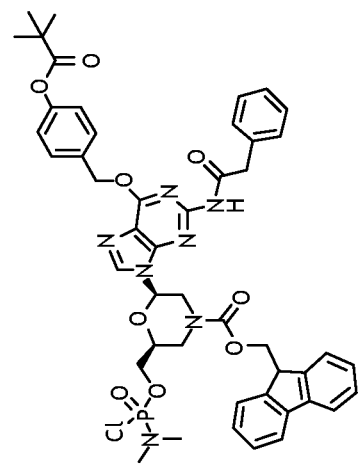
Figure 5B:
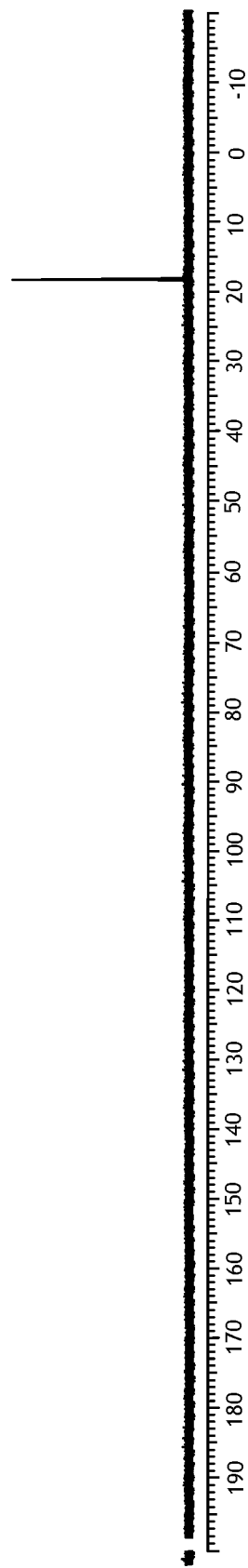

FIG. 5B shows the $^{13}$C NMR (CDCl3) of Fmoc Monomer G.

Figure 6:
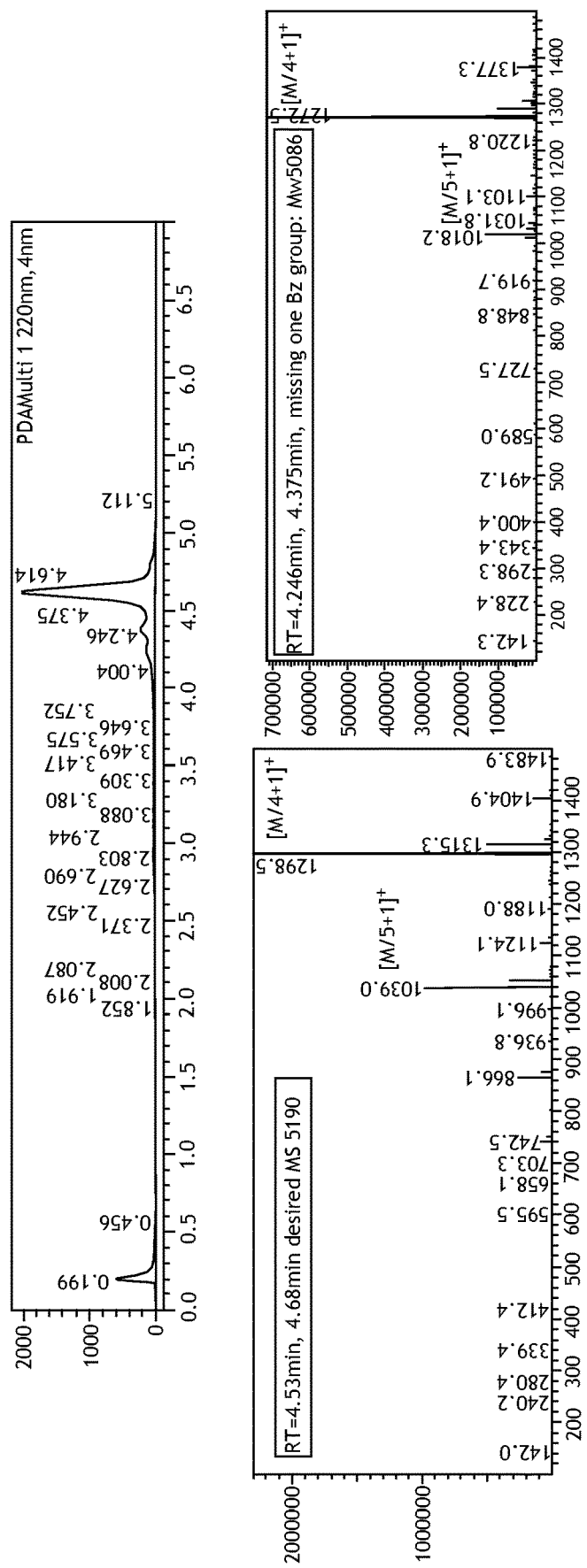

FIG. 6 provides LCMS data confirming the structure of a 12-mer PMO of the present disclosure.

Figure 7:
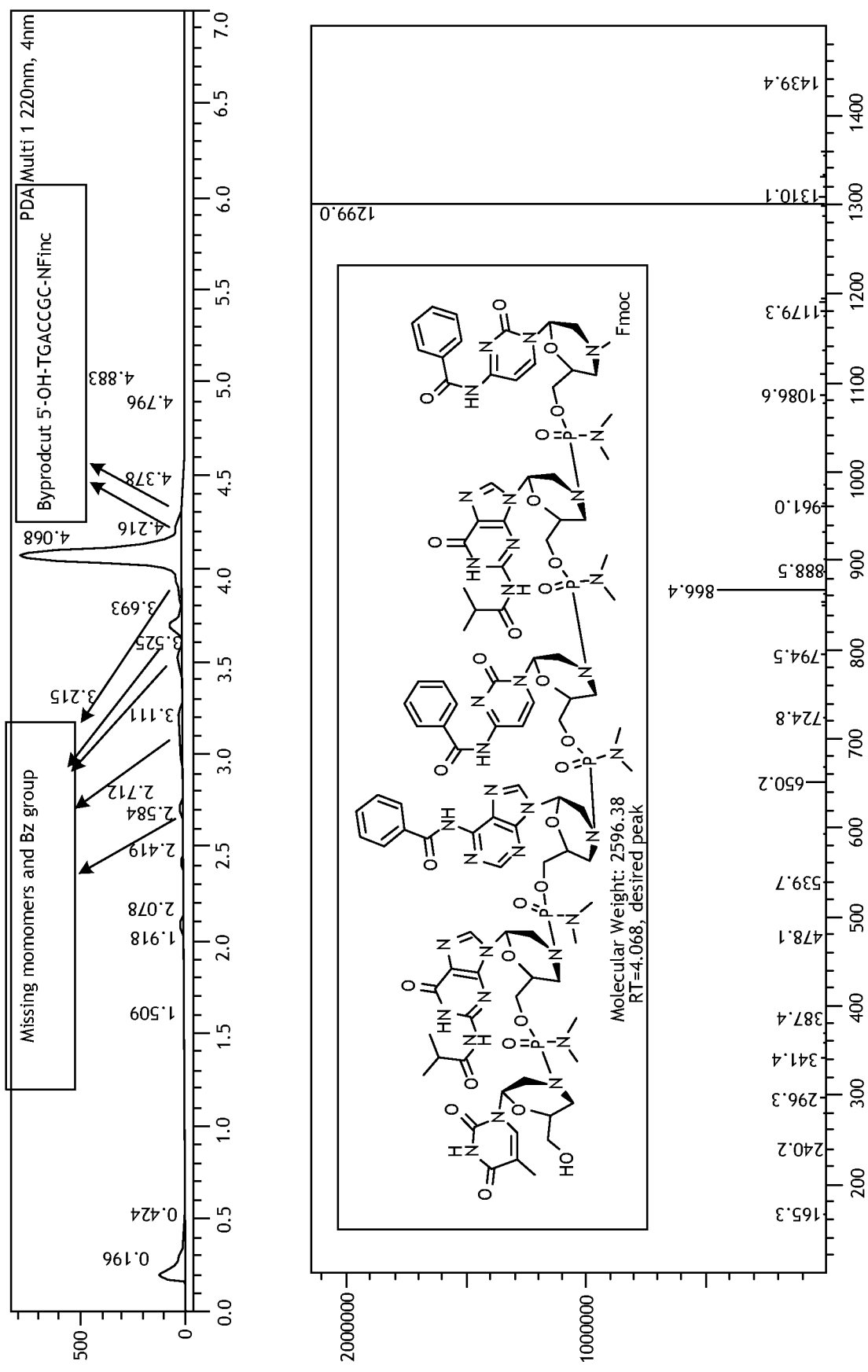

FIG. 7 provides LCMS data confirming the structure of a 5-mer PMO of the present disclosure.

Figure 8:
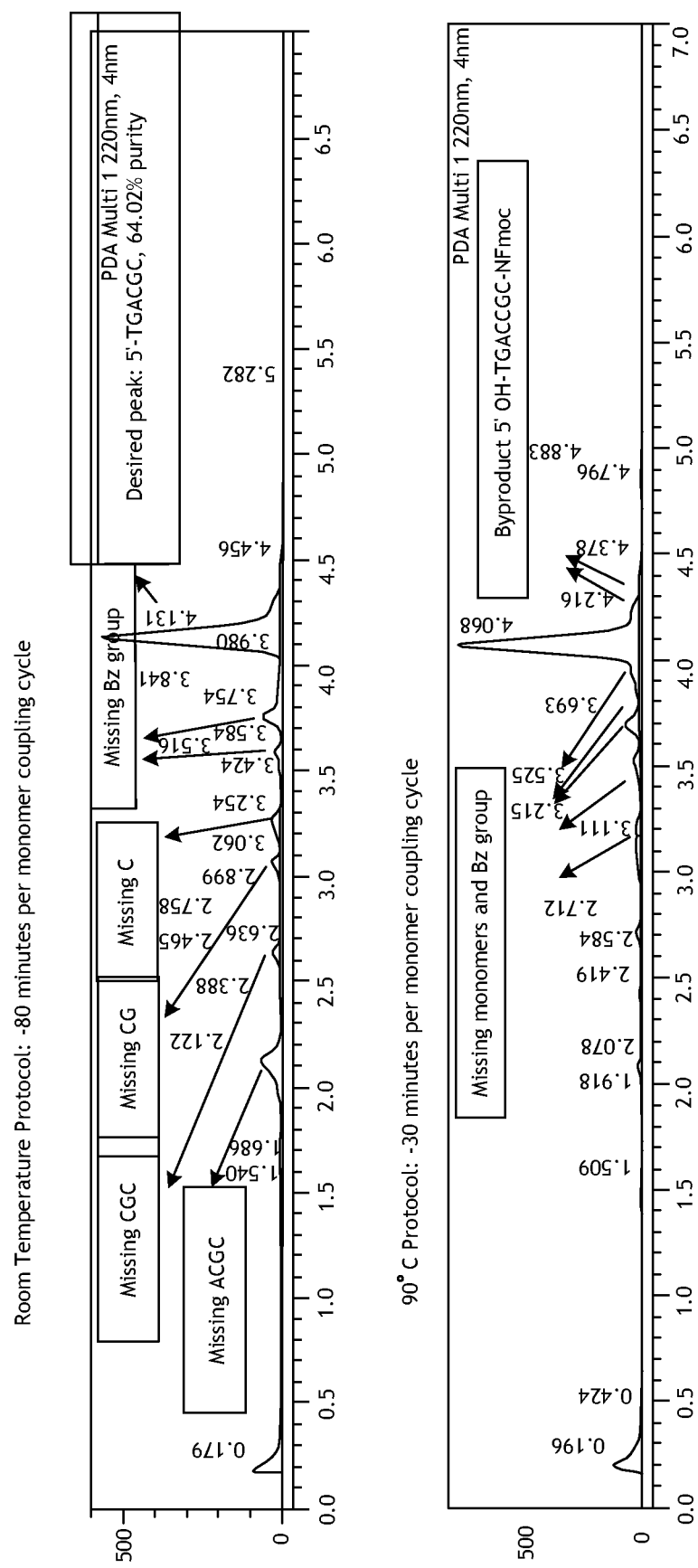

FIG. 8 provides a comparison of HPLC purity of 5-mer PMO product prepared by the room temperature protocol or the higher temperature protocol.

DETAILED DESCRIPTION

Definitions

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents, reference to "the component" includes mixtures of two or more such components, and the like.

As used herein, "about" means within 20%, 10%, or 5% of a given value or range. The allowable variation encompassed by "about" will depend upon the particular system under study, and can be readily appreciated by one of skill in the art.

As used herein "aromatic" refers to an unsaturated cyclic molecule having 4n+2π electrons, wherein n is any integer. The term "non-aromatic" refers to any unsaturated cyclic molecule which does not fall within the definition of aromatic.

"Alkyl", "alkyl group" or "alkyl chain" refer to a fully saturated, straight or branched hydrocarbon chain radical having from one to forty carbon atoms, and which is attached to the rest of the molecule by a single bond. Alkyls comprising any number of carbon atoms from 1 to 20 are included. An alkyl comprising up to 40 carbon atoms is a $C_1$-$C_{40}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, sec-propyl, n-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene", "alkylene group" or "alkylene chain" refer to a fully saturated, straight or branched divalent hydrocarbon chain radical, having from one to forty carbon atoms. Non-limiting examples of C2-C40 alkylene include ethylene, propylene, n-butylene, ethenylene, propenylene, n-butenylene, propynylene, n-butynylene, and the like. Unless stated otherwise specifically in the specification, an alkylene chain can be optionally substituted.

"Alkenyl", "alkenyl group" or "alkenyl chain" refer to a straight or branched hydrocarbon chain radical having from two to forty carbon atoms, and having one or more carbon-carbon double bonds. Each alkenyl group is attached to the rest of the molecule by a single bond. Alkenyl group comprising any number of carbon atoms from 2 to 40 are included. An alkenyl group comprising up to 40 carbon atoms is a $C_2$-$C_{40}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkenylene", alkenylene group" or "alkenylene chain" refers to a straight or branched divalent hydrocarbon chain radical, having from two to forty carbon atoms, and having one or more carbon-carbon double bonds. Non-limiting examples of $C_2$-$C_{40}$ alkenylene include ethene, propene, butene, and the like. Unless stated otherwise specifically in the specification, an alkenylene chain can be optionally.

"Alkoxy" or "alkoxy group" refer to the group —OR, where R is alkyl, alkenyl, alkynyl, cycloalkyl, or heterocyclyl as defined herein. Unless stated otherwise specifically in the specification, alkoxy can be optionally substituted.

"Acyl" or "acyl group" refer to the group —C(O)R, where R is hydrogen, alkyl, alkenyl, alkynyl, carbocyclyl, or heterocyclyl, as defined herein. Unless stated otherwise specifically in the specification, acyl can be optionally substituted.

"Alkylcarbamoyl" or "alkylcarbamoyl group" refer to the group —O—C(O)—NR$_a$R$_b$, where R$_a$ and R$_b$ are the same or different and independently an alkyl, alkenyl, alkynyl, aryl, heteroaryl, cycloalkyl, or heterocyclyl group, as defined herein, or $R_aR_b$ can be taken together to form a heterocyclyl group, as defined herein. Unless stated otherwise specifically in the specification, alkylcarbamoyl can be optionally substituted.

"Alkylcarboxamidyl" or "alkylcarboxyamidyl group" refer to the group —C(O)—$NR_aR_b$, where $R_a$ and $R_b$ are the same or different and independently an alkyl, alkenyl, alkynyl, aryl, heteroaryl, cycloalkyl, cycloalkenyl, cycloalkynyl, or heterocyclyl group, as defined herein, or $R_aR_b$ can be taken together to form a cycloalkyl group, as defined herein. Unless stated otherwise specifically in the specification, alkylcarboxamidyl can be optionally substituted.

"Aryl" refers to a hydrocarbon ring system radical comprising hydrogen, 6 to 18 carbon atoms and at least one aromatic ring. For purposes of this invention, the aryl radical can be a monocyclic, bicyclic, tricyclic or tetracyclic ring system, which can include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" is meant to include aryl radicals that are optionally substituted.

"Heteroaryl" refers to a 5- to 20-membered ring system radical comprising hydrogen atoms, one to thirteen carbon atoms, one to six heteroatoms selected from nitrogen, oxygen and sulfur, and at least one aromatic ring. For purposes of this invention, the heteroaryl radical can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group can be optionally substituted.

The term "substituted" used herein means any of the above groups (i.e., alkyl, alkenyl, alkynyl, cycloalkyl, cycloalkenyl, cycloalkynyl, heterocyclyl, aryl, heteroaryl, alkoxy, aryloxy, acyl, alkylcarbamoyl, alkylcarboxamidyl, alkoxycarbonyl, alkylthio, or arylthio) wherein at least one atom is replaced by a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more atoms are replaced with: —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted also means any of the above groups in which one or more hydrogen atoms are replaced with —C(=O)$R_g$, —C(=O)$OR_g$, —C(=O)$NR_gR_h$, —$CH_2SO_2R_g$, —$CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more atoms are replaced by an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. "Substituted" can also mean an amino acid in which one or more atoms on the side chain are replaced by alkyl, alkenyl, alkynyl, acyl, alkylcarboxamidyl, alkoxycarbonyl, carbocyclyl, heterocyclyl, aryl, or heteroaryl. In addition, each of the foregoing substituents can also be optionally substituted with one or more of the above substituents.

A "morpholino oligomer" refers to a polymeric molecule having a backbone which supports bases capable of hydrogen bonding to polynucleotides, wherein the polymer contains at least one ring containing a nitrogen with coupling through the ring nitrogen. In embodiments, the morpholino oligomer is composed of "morpholino subunit" structures, such as shown below, which in the oligomer are linked together by (thio)phosphorodiamidate linkages, joining the morpholino nitrogen of one subunit to the 5' exocyclic carbon of an adjacent subunit. Each subunit includes a purine or pyrimidine base-pairing moiety Pi which is effective to bind, by base-specific hydrogen bonding, to a base in a polynucleotide.

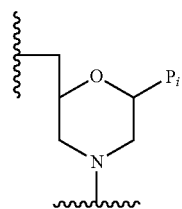

Morpholino oligomers are detailed, for example, in U.S. Pat. Nos. 5,698,685, 5,217,866, 5,142,047, 5,034,506, 5,166,315, 5,185,444, 5,521,063, and 5,506,337, which are each incorporated by reference herein in their entireties.

A "phosphorodiamidate" group comprises phosphorus having two attached oxygen atoms and two attached nitrogen atoms, and herein may also refer to phosphorus having one attached oxygen atom and three attached nitrogen atoms. In the intersubunit linkages of the oligomers described herein, one nitrogen may be pendant to the backbone chain, and the second nitrogen may be the ring nitrogen in a morpholino ring structure, as shown in formula II below. Alternatively or in addition, a nitrogen may be present at the 5'-exocyclic carbon, as shown in formulas III and IV below.

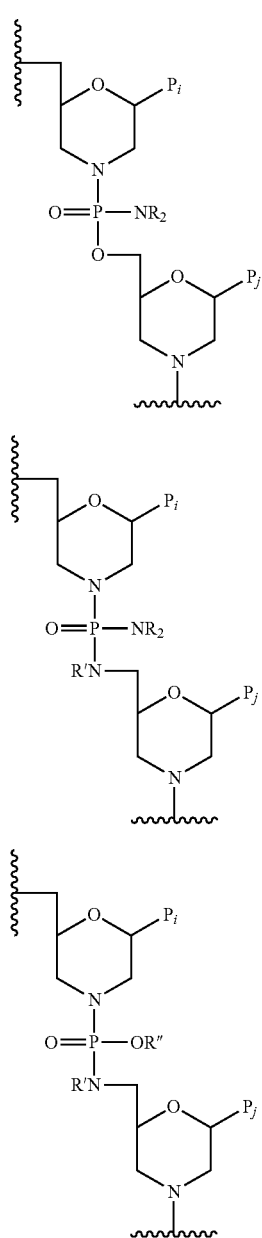

In a thiophosphorodiamidate linkage, one oxygen atom, for example, an oxygen pendant to the backbone in the oligomers described herein, is replaced with sulfur.

A "solid-phase-supported morpholino subunit" can be the first or any subsequent morpholino subunit monomer incorporated into a morpholino oligomer by solid-phase stepwise synthesis as described herein. The subunit is attached to the solid support, or to a growing oligomer chain on the solid support, via its 5' exocyclic carbon. "Base-protected" refers to protection of the base-pairing groups, e.g. purine or pyrimidine bases, on the morpholino subunits with protecting groups suitable to prevent reaction or interference with the base-pairing groups during stepwise oligomer synthesis.

An "activated phosphoramidate group" is a chlorophosphoramidate group, having substitution at nitrogen which is desired in the eventual phosphoramidate linkage in the oligomer. An example is (dimethylamino)chlorophosphoramidate, i.e. —O—P(=O)(NMe$_2$)Cl.

Compounds of the Disclosure

As indicated in U.S. Pat. No. 8,076,476, which is incorporated herein by reference, the functional groups on the heterocyclic bases may be masked to prevent cross-reactivity in the synthetic transformations used in conventional oligonucleotide synthesis. Still, when the 5'-hydroxyl of various N-tritylated morpholino monomers is reacted with a suitable phosphoramido dichloridate to form an activated subunit, the crude activated subunit is generally contaminated with a high level of by-products under large scale conditions (50-100 gallon reactor). Following chromatographic purification, the activated subunit is isolated in about 50% yield for A, C, I, T, U and their protected forms, but only in about 5% yield for the activated singly protected G subunit, which is believed to be due to the presence of the unprotected O6 oxygen.

The O6-unprotected guanine subunit also gives rise to side reactions at the oligomer stage. For example, the O6 oxygen can react with activated subunit during coupling steps, to form O6-phosphorylated or derivative species, and during final cleavage of the base protecting groups with ammonia, ammonia can react at C6 to displace these species, giving a diaminopurine derivative. Such impurities are difficult to remove by chromatography, and cause a large loss in yield.

Various protection schemes have been proposed in the art to reduce side reactions of unprotected guanine O6 positions in conventional oligonucleotide synthesis. However, these protocols are largely unsuccessful when applied to PMO synthesis.

Due to the specific challenges of PMO chemistry, a base protecting group should fill several requirements in order to provide high yielding and efficient preparation of the target molecules. The protecting group should be readily introduced onto the heterocyclic moiety and thereafter be stable to subunit activation and purification conditions, and solid phase synthesis. The protecting group should not be reactive with the morpholino amine moiety of the growing chain, and should allow the activated morpholino subunit to couple cleanly with the growing oligomer chain. In addition, the protecting group should be cleaved without introducing new impurities. If crystalline subunit derivatives are provided, the need for chromatographic purification prior to activation can be avoided. Lastly the protecting group should be compatible with reaction conditions that facilitate the formation of pure material over shorter reaction times.

The protecting groups reported in the literature for protected guanosines, as used for nucleic acid synthesis, did not adequately meet these criteria. Thus, a new protecting strategy was required for morpholino G subunits. As described herein, use of the 4-(pivaloyloxy)benzyloxy group, and the like, at the O6 position, in the context of Fmoc-protected morpholino monomers was found to meet the above criteria. Advantageously, protecting morpholino G subunits at the O6 position, in addition to the N2 position (referred to herein as "di-protected Fmoc morpholino monomer G" or "bis-protected Fmoc morpholino monomer G"), improved efficiency, by improving purity and reducing overall synthesis time.

In embodiments, the present disclosure provides a compound of Formula (I):

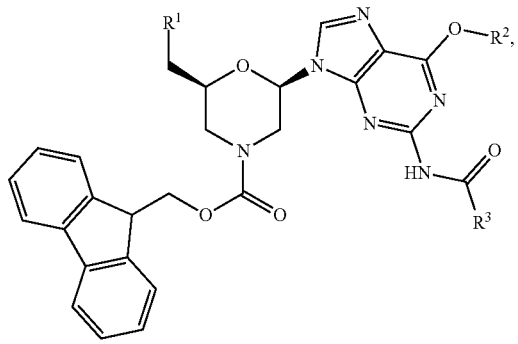

wherein:
R¹ is a protected or unprotected hydroxyl group, a chlorophosphoramidate group, a phosphoramidate linkage to the morpholino ring nitrogen of a morpholino subunit monomer, a phosphoramidate linkage to the morpholino ring nitrogen of a morpholino subunit in a morpholino oligomer, or a linkage to a solid support;
R² is a protecting group; and
R³ is a protecting group.

In embodiments, the present disclosure provides a compound of Formula (I):

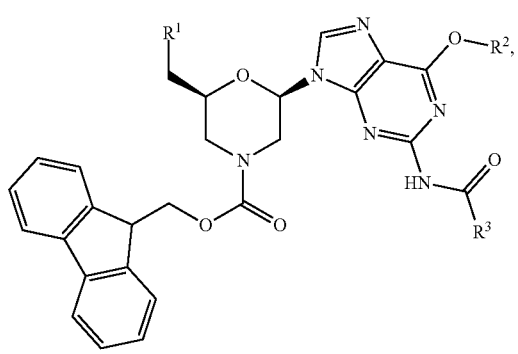

wherein:
R¹ is a protected or unprotected hydroxyl group, a chlorophosphoramidate group, a phosphoramidate linkage to the morpholino ring nitrogen of a morpholino subunit monomer, a phosphoramidate linkage to the morpholino ring nitrogen of a morpholino subunit in a morpholino oligomer, or a linkage to a solid support;
R² is H, alkyl or alkylenearyl, each of which is optionally substituted; and
R³ is alkyl, alkylenearyl (e.g., —CH₂Ph), or alkylenearyloxy (e.g., —CH₂OPh), each of which is optionally substituted,
provided that when R² is H, R³ is not —CH(CH₃)₂.

In embodiments, the present disclosure provides a compound of Formula (I):

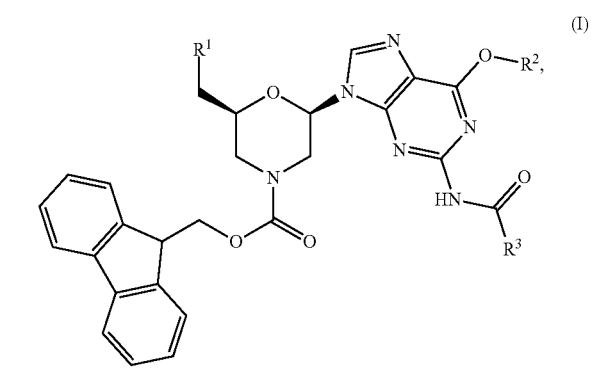

wherein:
R¹ is a protected or unprotected hydroxyl group, a chlorophosphoramidate group, a phosphoramidate linkage to the morpholino ring nitrogen of a morpholino subunit monomer, a phosphoramidate linkage to the morpholino ring nitrogen of a morpholino subunit in a morpholino oligomer, or a linkage to a solid support;
R² is alkyl or alkylenearyl, each of which is optionally substituted; and
R³ is alkyl, alkylenearyl (e.g., —CH₂Ph), or alkylenearyloxy (e.g., —CH₂OPh), each of which is optionally substituted.

In embodiments, R¹ is a protected or unprotected hydroxyl group, a chlorophosphoramidate group, an H-phosphonate group, a phosphoramidate linkage to the morpholino ring nitrogen of a morpholino subunit monomer, a phosphoramidate linkage to the morpholino ring nitrogen of a morpholino subunit in a morpholino oligomer, or a linkage to a solid support. In embodiments, R¹ is —OH, chlorophosphoramidate group, or a linkage to a solid support.

In embodiments, R¹ is a chlorophosphoramidate group. In embodiments, the chlorophosphoramidate group is —P(O)(Cl)N(C₁₋₅alkyl)₂. In embodiments, the chlorophosphoramidate group is —P(=O)(Cl)N(CH₃)₂.

In embodiments, R¹ is an H-phosphonate group. In embodiments, the H-phosphonate group is —P(O)(H)O⁻ ⁺NH(C₁₋₅alkyl)₃. In embodiments, the H-phosphonate group is —P(O)(H)O⁻ ⁺NH(Et)₃.

In embodiments, R¹ is a linkage to a solid support. In embodiments, the linkage comprises optionally substituted trityl, aminomethyl (e.g., aminomethyl polystyrene resin), p-alkoxybenzyl alcohol (e.g., Wang resin), 4-(4-hydroxymethyl-3-methoxyphenoxy)butyric acid (e.g., HMPB resin), 4-[(2,4-dimethoxyphenyl)(amino)methyl]phenoxyacetic acid (e.g., Rink amide resin), or (RS)-2-{[5-(Fmoc-amino)dibenzo[a,d]cycloheptane-2-yl]oxy}acetic acid (e.g., Ramage resin), each of which is optionally functionalized with a terminal succinic acid.

In embodiments, R¹ is a protected hydroxyl group. In embodiments, the hydroxyl protecting group is a protecting group disclosed in "Protection for the Hydroxyl Group, Including 1,2- and 1,3-Diols." In *Greene's Protective Groups in Organic Synthesis*, (2014). P. G. M. Wuts (Ed.), which is incorporated by reference herein in its entirety. In embodiments, the protecting group is a silyl protecting group. In embodiments, the silyl protecting group is a tert-butyldimethylsilyl (TBS) group.

In embodiments, R¹ is a phosphoramidate linkage to the morpholino ring nitrogen of a morpholino subunit monomer. In embodiments, R¹ is a phosphoramidate linkage to the morpholino ring nitrogen of a morpholino subunit in a morpholino oligomer. In embodiments, the phosphoramidate linkage is —P(O)N(C$_{1-5}$alkyl)$_2$-. In embodiments, the phosphoramidate linkage is —P(O)N(CH$_3$)$_2$—.

In embodiments, R$^2$ is a protecting group. In embodiments, the protecting group is a protecting group disclosed in "Protection for the Hydroxyl Group, Including 1,2- and 1,3-Diols" in *Greene's Protective Groups in Organic Synthesis*, (2014). P. G. M. Wuts (Ed.), which is incorporated by reference herein in its entirety. In embodiments, R$^2$ is alkyl or alkylenearyl, each of which is optionally substituted. In embodiments, R$^2$ is alkyl. In embodiments, the alkyl is a C$_{1-5}$alkyl. In embodiments, R$^2$ is alkylenearyl. In embodiments, the alkylenearyl is a C$_{1-3}$alkylenearyl. In embodiments, the aryl is an optionally substituted phenyl. In embodiments, R$^2$ is 4-nitrophenethyl (NPE). In embodiments, the optional substituent is an ester, carbonate, carbamate, or the like. In embodiments, the optional substituent is in the para position of the phenyl ring. In embodiments, R$^2$ is

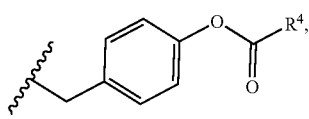

wherein R$^4$ is alkyl, aryl, —CH$_2$aryl or —N(C$_{1-5}$alkyl)$_2$. In embodiments, R$^2$ is

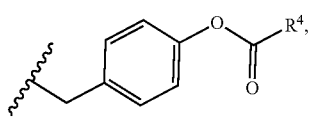

wherein R$^4$ is alkyl, aryl, or —CH$_2$aryl. In embodiments, the alkyl is a C$_{1-5}$alkyl. In embodiments, the alkyl is methyl, ethyl, n-propyl, n-butyl, t-butyl, isoamyl, or neopentyl. In embodiments, the alkyl is t-butyl. In embodiments, the aryl is an optionally substituted phenyl. In embodiments, R$^2$ is

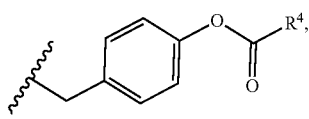

wherein R$^4$ is t-butyl, benzyl, or phenyl. In embodiments, R$^2$ is

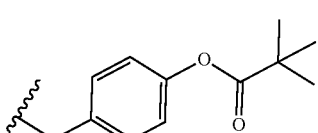

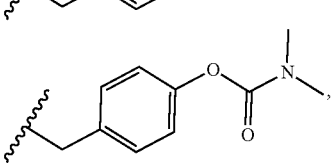

-continued

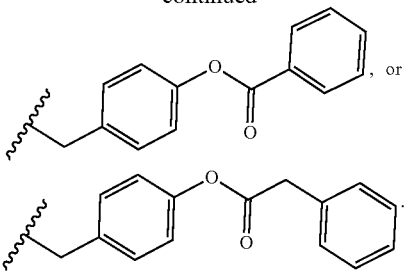

In embodiments, R$^3$ is a protecting group. In embodiments, the protecting group is a protecting group disclosed in "Protection for the Hydroxyl Group, Including 1,2- and 1,3-Diols" in *Greene's Protective Groups in Organic Synthesis*, (2014). P. G. M. Wuts (Ed.), which is incorporated by reference herein in its entirety. In embodiments, R$^3$ is alkyl. In embodiments, the alkyl is a C$_{1-5}$alkyl. In embodiments, the alkyl is —CH$_3$, —CH$_2$CH$_3$, or —CH(CH$_3$)$_2$. In embodiments, R$^3$ is alkylenearyl. In embodiments, R$^3$ is —CH$_2$aryl. In embodiments, R$^3$ is —CH$_2$Ph. In embodiments, R$^3$ is alkylenearyloxy. In embodiments, R$^3$ is —CH$_2$aryloxy. In embodiments, R$^3$ is —CH$_2$OPh. In embodiments, R$^3$ is —CH$_2$Ph or —CH(CH$_3$)$_2$. In embodiments, R$^3$ is C$_{1-5}$alkyl (e.g., —CH$_3$, —CH$_2$CH$_3$, or —CH(CH$_3$)$_2$), —CH$_2$aryl (e.g., —CH$_2$Ph), or —CH$_2$aryloxy (e.g., —CH$_2$OPh).

In embodiments, R$^1$ is a protected or unprotected hydroxyl group, a chlorophosphoramidate group, a phosphoramidate linkage to the morpholino ring nitrogen of a morpholino subunit monomer, a phosphoramidate linkage to the morpholino ring nitrogen of a morpholino subunit in a morpholino oligomer, or a linkage to a solid support; R$^2$ is

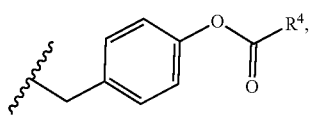

wherein R$^4$ is alkyl, aryl, —CH$_2$aryl or —N(C$_{1-5}$alkyl)$_2$; and R$^3$ is C$_{1-5}$alkyl (e.g., —CH$_3$, —CH$_2$CH$_3$, or —CH(CH$_3$)$_2$), —CH$_2$aryl (e.g., —CH$_2$Ph), or —CH$_2$aryloxy (e.g., —CH$_2$OPh).

In embodiments, R$^1$ is —OH, chlorophosphoramidate group, or a linkage to a solid support; R$^2$ is

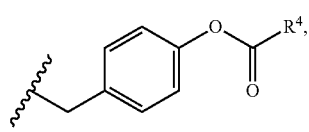

wherein R$^4$ is alkyl, aryl, —CH$_2$aryl or —N(C$_{1-5}$alkyl)$_2$; and R$^3$ is C$_{1-5}$alkyl (e.g., —CH$_3$, —CH$_2$CH$_3$, or —CH(CH$_3$)$_2$), —CH$_2$aryl (e.g., —CH$_2$Ph), or —CH$_2$aryloxy (e.g., —CH$_2$OPh).

In embodiments, the compound of Formula (I) excludes any compound disclosed in U.S. Pat. No. 8,076,476. In embodiments, the compound of Formula (I) excludes any compound disclosed in Ghosh, U. et al. "Synthesis of Phosphoramidate Morpholino Oligonucleotides Using Trityl and Fmoc Chemistry-A New Method Amendable to Automated Synthesizer" *ChemRxiv*, posted Jun. 8, 2020. In embodiments, the compound of Formula (I) excludes any compound disclosed in U.S. Patent Pub. No. 2021/0130379.

In embodiments, when $R^2$ is H, $R^3$ is not —CH(CH$_3$)$_2$.

In embodiments, the compound of Formula (I) is:

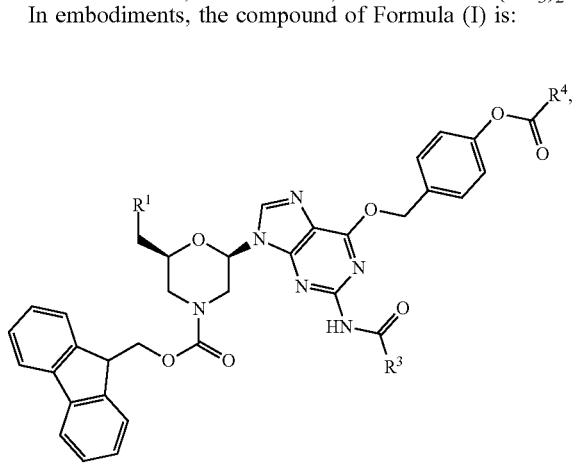

wherein $R^1$, $R^3$, and $R^4$ are as defined above.

In embodiments, the compound of Formula (I) is:

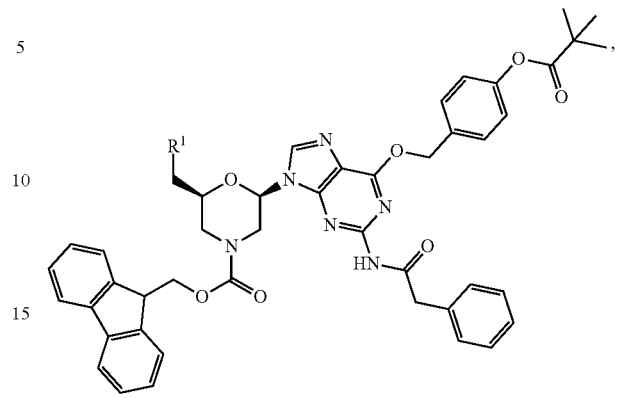

wherein $R^1$ is as defined above.

In embodiments, the solid-supported morpholino monomer has the structure of Formula (IA)-Formula (IF):

(IA)

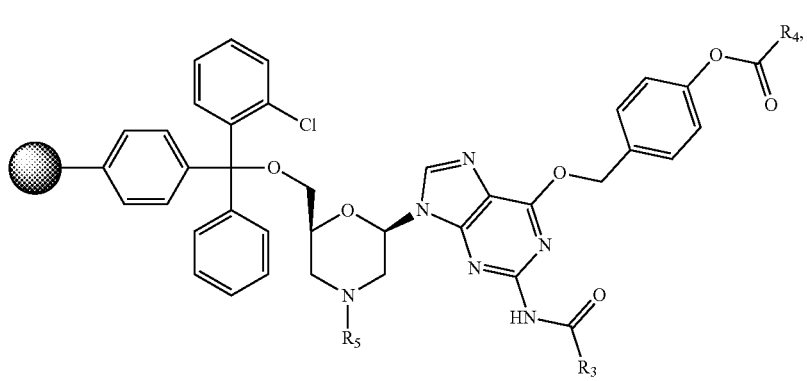

(IB)

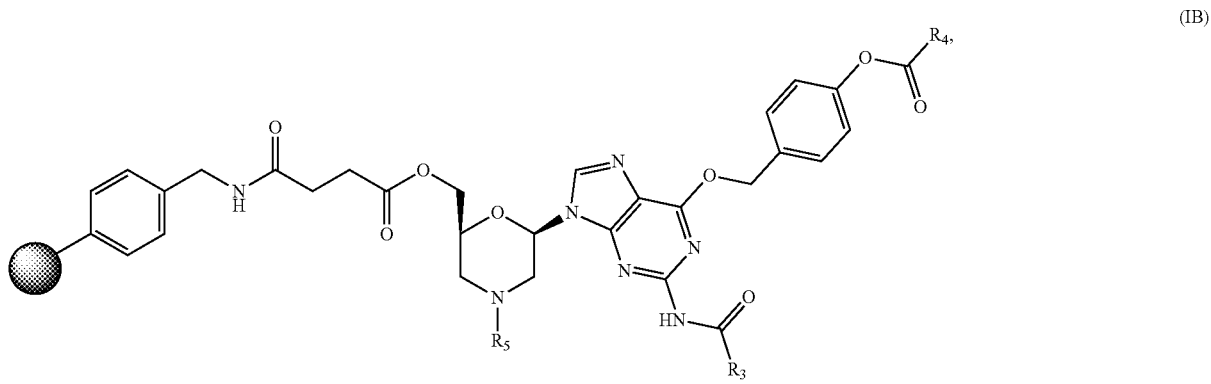

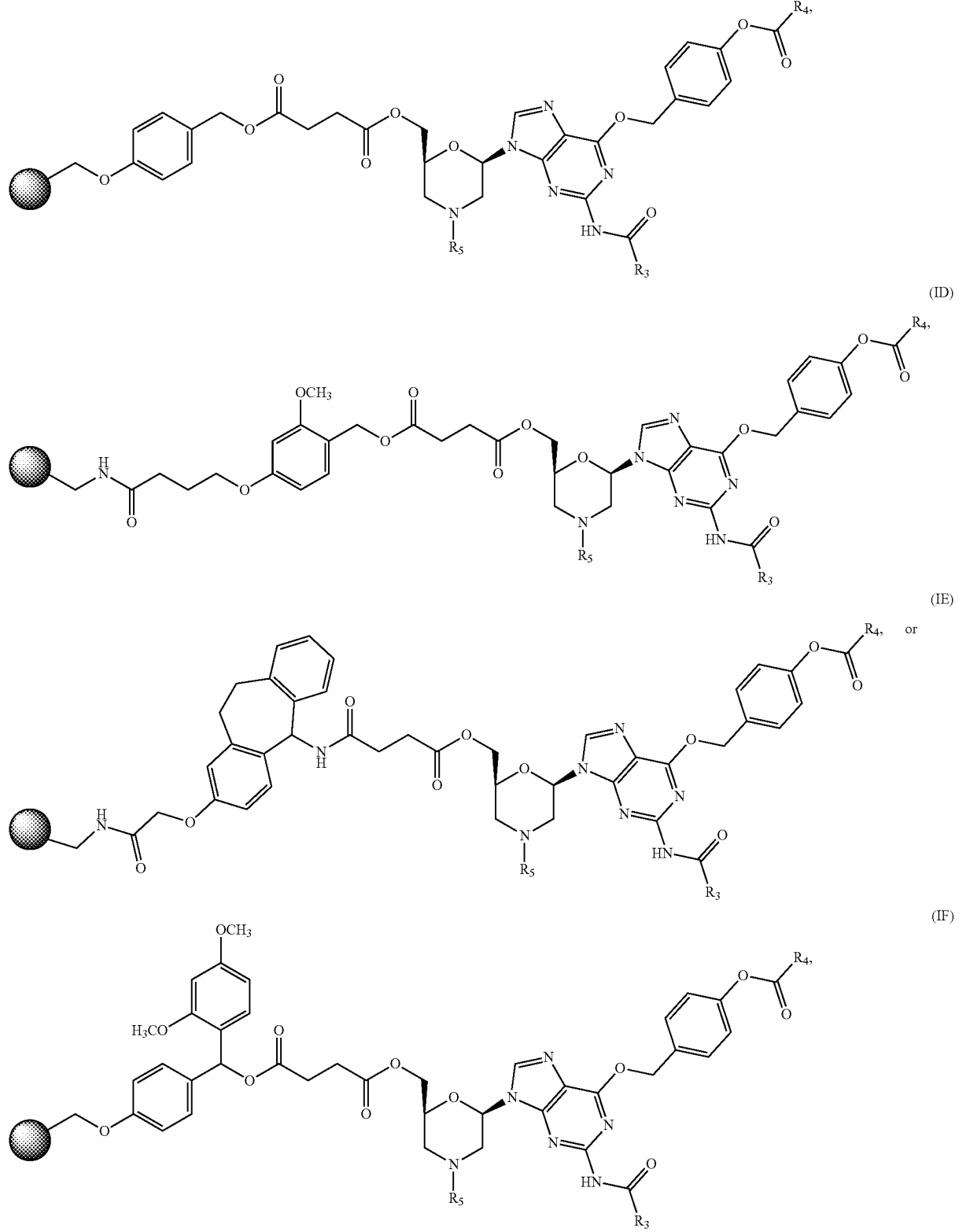
wherein:
R³ and R⁴ are as defined above;
R⁵ is H or Fmoc; and
⬤— is a solid support.

In embodiments, the solid-supported morpholino monomer has the structure of Formula (IA):

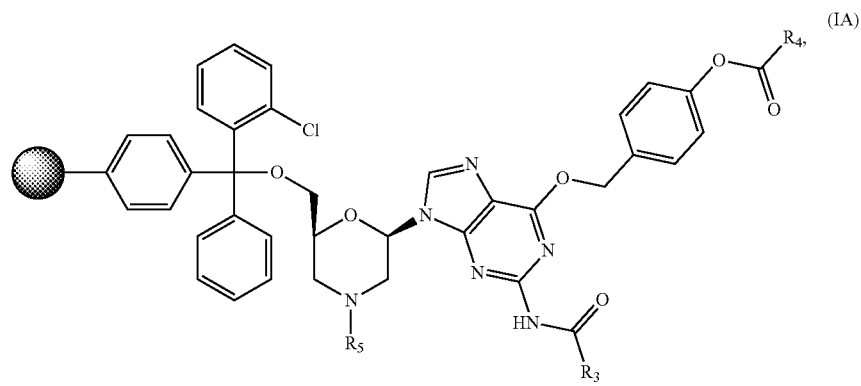

wherein:

$R^3$ and $R^4$ are as defined above;

$R^5$ is H or Fmoc; and

⬤— is a solid support.

In embodiments, the morpholino subunit monomer comprising an Fmoc-protected morpholino ring nitrogen and an activated phosphoramidate group on a 5'-exocyclic carbon has the structure of Formula (IA1) or Formula (IB1):

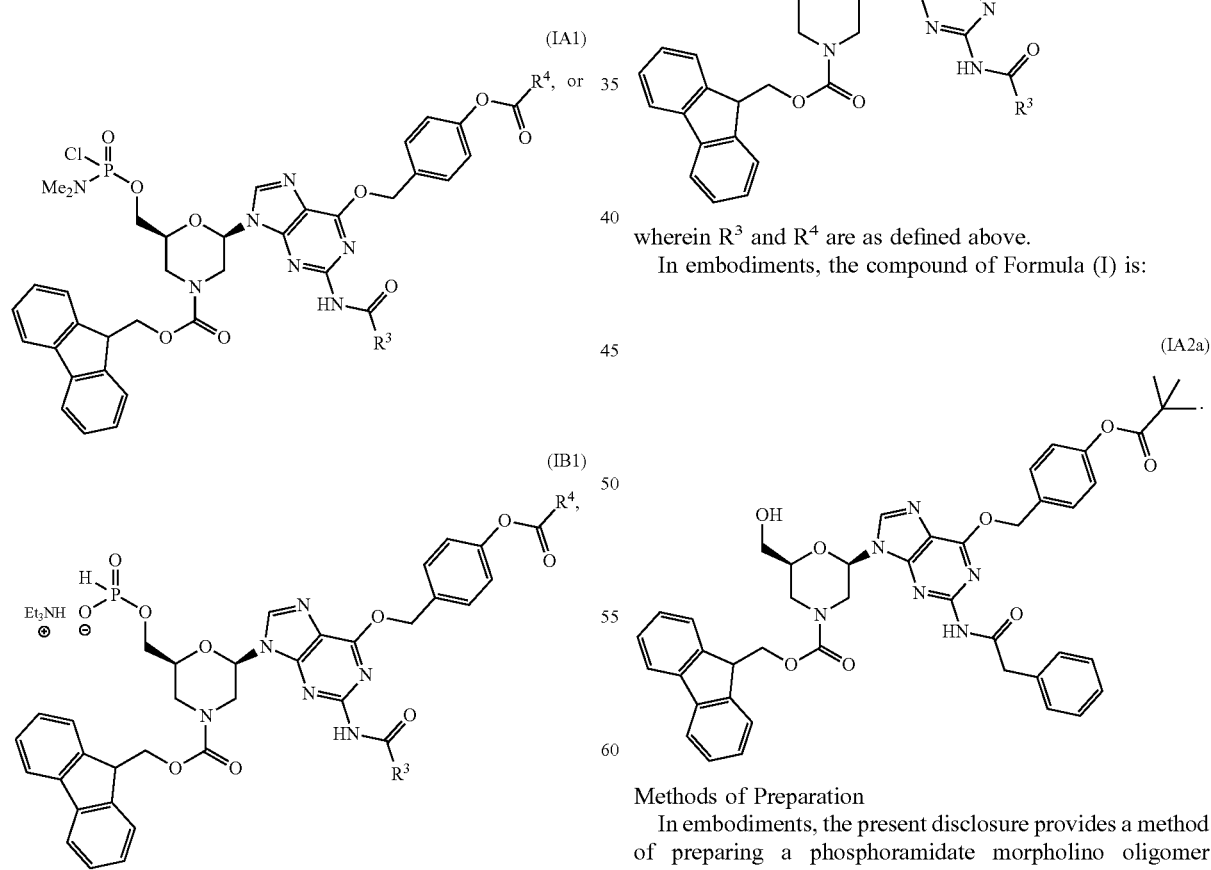

wherein $R^3$ and $R^4$ are as defined above.

In embodiments, the compound of Formula (I) is:

wherein $R^3$ and $R^4$ are as defined above.

In embodiments, the compound of Formula (I) is:

Methods of Preparation

In embodiments, the present disclosure provides a method of preparing a phosphoramidate morpholino oligomer (PMO), the method comprising: coupling a morpholino subunit monomer or an oligomer thereof with a monomer of Formula (I) having the structure:

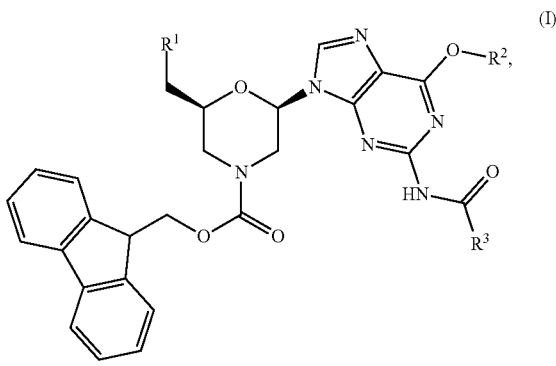

(I)

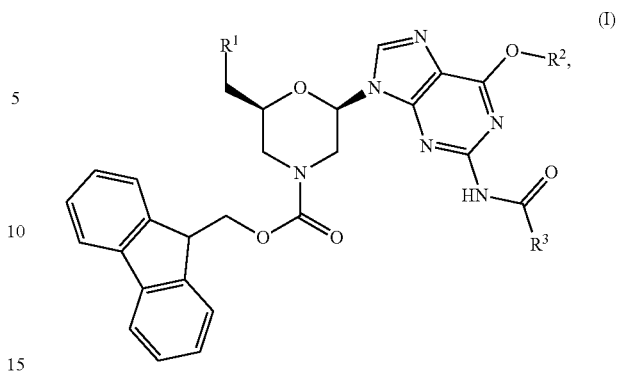

(I)

wherein:

R¹ is a protected or unprotected hydroxyl group, a chlorophosphoramidate group, a phosphoramidate linkage to the morpholino ring nitrogen of a morpholino subunit monomer, a phosphoramidate linkage to the morpholino ring nitrogen of a morpholino subunit in a morpholino oligomer, or a linkage to a solid support;

R² is H, alkyl or alkylenearyl, each of which is optionally substituted; and

R³ is alkyl, alkylenearyl (e.g., —CH₂Ph), or alkylenearyloxy (e.g., —CH₂OPh), each of which is optionally substituted, provided that when R² is H, R³ is not —CH(CH₃)₂.

In embodiments, the present disclosure provides a method of preparing a phosphoramidate morpholino oligomer (PMO), comprising:

a) coupling a solid-supported morpholino monomer comprising an unprotected ring nitrogen with a first morpholino subunit monomer comprising a fluorenylmethyoxycarbonyl (Fmoc)-protected morpholino ring nitrogen and an activated phosphoramidate group on a 5'-exocyclic carbon, thereby forming a first phosphorodiamidate linkage between the 5'-exocyclic carbon of the first morpholino subunit monomer and the unprotected morpholino ring nitrogen of the solid-supported morpholino subunit monomer;

(b) deprotecting the Fmoc-protected morpholino ring nitrogen to form a product comprising an unprotected morpholino ring nitrogen;

(c) optionally coupling the product from step (b) with a second morpholino subunit monomer comprising an Fmoc-protected morpholino ring nitrogen and an activated phosphoramidate group on a 5'-exocyclic carbon, thereby forming a second phosphorodiamidate linkage between the 5'-exocyclic carbon of the second morpholino subunit monomer and the unprotected morpholino ring nitrogen of the product from step (b); and (d) optionally repeating steps (b) and (c) one or more times;

wherein at least one of the first morpholino subunit monomer, the second morpholino subunit monomer, a further morpholino subunit monomer, or the solid-phase-supported morpholino subunit monomer is a protected guanine morpholino compound having the structure of Formula (I):

wherein:

R¹ is a protected or unprotected hydroxyl group, a chlorophosphoramidate group, a phosphoramidate linkage to the morpholino ring nitrogen of a morpholino subunit monomer, a phosphoramidate linkage to the morpholino ring nitrogen of a morpholino subunit in a morpholino oligomer, or a linkage to a solid support;

R² is alkyl or alkylenearyl, each of which is optionally substituted; and

R3 is alkyl, alkylenearyl, or alkylenearyloxy, each of which is optionally substituted.

In embodiments, the method further comprises the cleaving PMO from solid support. In embodiments, cleavage from the solid support includes the treating the solid-supported PMO with a solution of trifluoroacetic acid (TFA) in DCM.

In embodiments, R¹ is —OH, chlorophosphoramidate group, or a linkage to a solid support. In embodiments, R¹ is a chlorophosphoramidate group. In embodiments, the chlorophosphoramidate group is —P(O)(CON(C₁₋₅alkyl)₂. In embodiments, the chlorophosphoramidate group is —P(=O)(Cl)N(CH₃)₂.

In embodiments, R¹ is a protected hydroxyl group. In embodiments, the hydroxyl protecting group is a protecting group disclosed in "Protection for the Hydroxyl Group, Including 1,2- and 1,3-Diols" in *Greene's Protective Groups in Organic Synthesis*, (2014). P. G. M. Wuts (Ed.), which is incorporated by reference herein in its entirety. In embodiments, the protecting group is a silyl protecting group. In embodiments, the silyl protecting group is a tert-butyldimethylsilyl (TBS) group.

In embodiments, R¹ is a linkage to a solid support. In embodiments, the linkage comprises trityl, aminomethyl (e.g., aminomethyl polystyrene resin), p-alkoxybenzyl alcohol (e.g., Wang resin), 4-(4-hydroxymethyl-3-methoxyphenoxy)butyric acid (e.g., HMPB resin), 4-[(2,4-dimethoxyphenyl)(amino)methyl]phenoxyacetic acid (e.g., Rink amide resin), or (RS)-2-{[5-(Fmoc-amino)dibenzo[a,d]cycloheptane-2-yl]oxy}acetic acid (e.g., Ramage resin), each of which is optionally functionalized with a terminal succinic acid.

In embodiments, R¹ is a phosphoramidate linkage to the morpholino ring nitrogen of a morpholino subunit monomer. In embodiments, R¹ is a phosphoramidate linkage to the morpholino ring nitrogen of a morpholino subunit in a morpholino oligomer. In embodiments, the phosphoramidate linkage is —P(O)N(C₁₋₅alkyl)₂-. In embodiments, the phosphoramidate linkage is —P(O)N(CH₃)₂—.

In embodiments, R² is alkyl or alkylenearyl, each of which is optionally substituted. In embodiments, R² is alkyl. In embodiments, the alkyl is a C₁₋₅alkyl. In embodiments, $R^2$ is alkylenearyl. In embodiments, the alkylenearyl is a $C_{1-3}$alkylenearyl. In embodiments, the aryl is an optionally substituted phenyl. In embodiments, the optional substituent is an ester, carbonate, carbamate, or the like. In embodiments, the optional substituent is in the para position of a phenyl ring. In embodiments, $R^2$ is

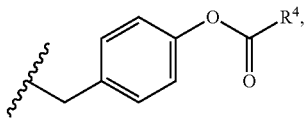

wherein $R^4$ is alkyl, aryl, —$CH_2$aryl or —$N(C_{1-5}alkyl)_2$. In embodiments, $R^2$ is

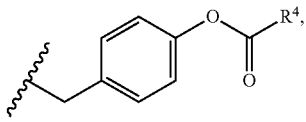

wherein $R^4$ is alkyl, aryl, or —$CH_2$aryl. In embodiments, the alkyl is a $C_{1-5}$alkyl. In embodiments, the alkyl is methyl, ethyl, propyl, n-butyl, t-butyl, isoamyl, or neopentyl. In embodiments, the alkyl is t-butyl. In embodiments, the aryl is an optionally substituted phenyl. In embodiments, $R^2$ is

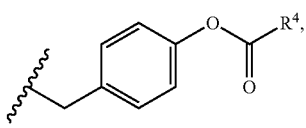

wherein $R^4$ is t-butyl, benzyl, or phenyl. In embodiments, $R^2$ is

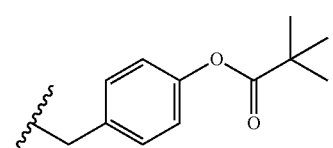

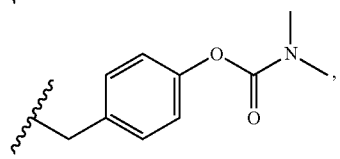

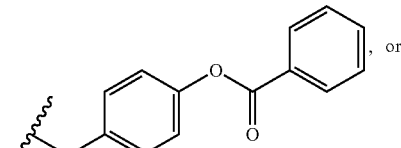

, or

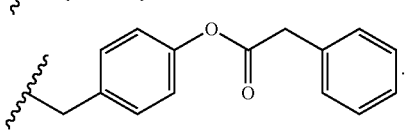

.

In embodiments, $R^2$ is

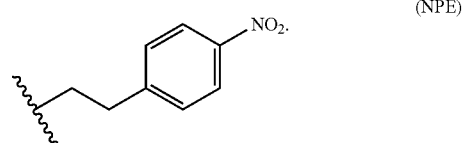 [SMILES: *CCc1ccc([N+](=O)[O-])cc1]

(NPE)

In embodiments, $R^3$ is alkyl. In embodiments, the alkyl is a $C_{1-5}$alkyl. In embodiments, $R^3$ is alkylenearyl. In embodiments, $R^3$ is —$CH_2$aryl. In embodiments, $R^3$ is —$CH_2$Ph. In embodiments, $R^3$ is alkylenearyloxy. In embodiments, $R^3$ is —$CH_2$aryloxy. In embodiments, $R^3$ is —$CH_2$OPh. In embodiments, $R^3$ is —$CH_2$Ph or —$CH(CH_3)_2$.

In embodiments, the compound of Formula (I) excludes any compound disclosed in U.S. Pat. No. 8,076,476. In embodiments, the compound of Formula (I) excludes any compound disclosed in Ghosh, U. et al. "Synthesis of Phosphoramidate Morpholino Oligonucleotides Using Trityl and Fmoc Chemistry-A New Method Amendable to Automated Synthesizer" *ChemRxiv*, posted Jun. 8, 2020. In embodiments, the compound of Formula (I) excludes any compound disclosed in U.S. Patent Pub. No. 2021/0130379.

In embodiments, when $R^2$ is H, $R^3$ is not —$CH(CH_3)_2$.

In embodiments, the compound of Formula (I) is:

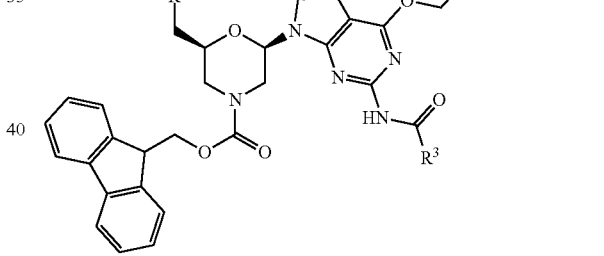

wherein $R^1$, $R^3$ and $R^4$ are as defined above.

In embodiments, the compound of Formula (I) is:

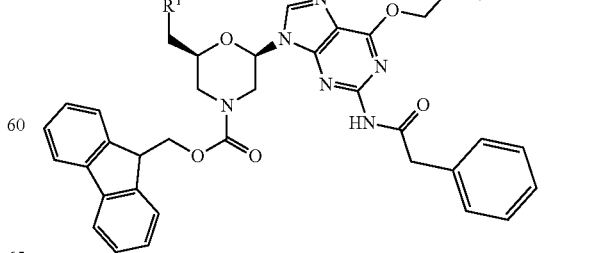

wherein $R^1$ is as defined above.

In embodiments, the solid-supported morpholino monomer has a structure selected from:
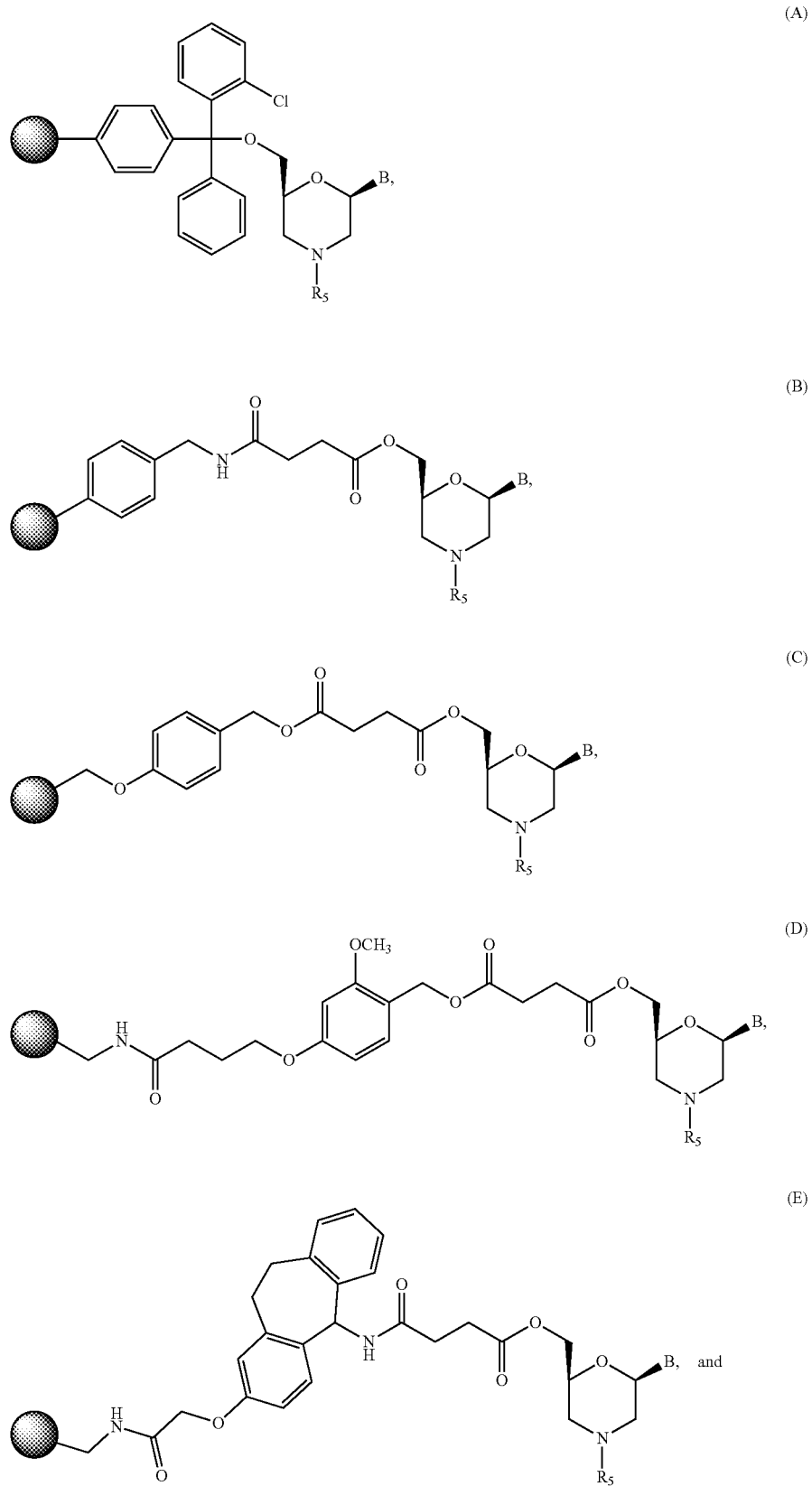

-continued (F)

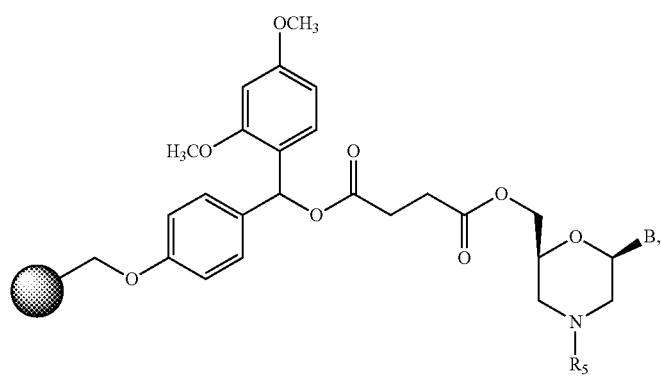

wherein:
R⁵ is H or Fmoc;
B is a nucleobase selected from the guanine (Formula (IA-IF)), adenine (Formula (IIA-IIF)), cytosine (Formula (IIIA-IIIF)), and thymine (Formula (IVA-IVF)); and ⬤— is a solid support.

In embodiments, the solid-supported morpholino monomer has the structure:

(A)

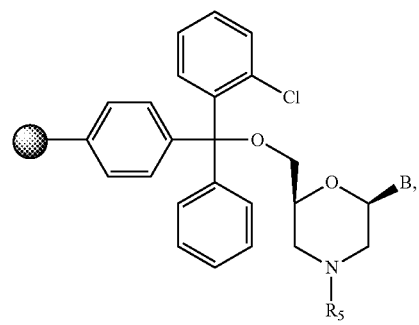

wherein:
R⁵ is H or Fmoc;
B is a nucleobase selected from guanine (Formula (IA)), adenine (Formula (IIA)), cytosine (Formula (MA)), and thymine (Formula (IVA)); and ⬤— is a solid support.

In embodiments, the morpholino subunit monomer comprising an Fmoc-protected morpholino ring nitrogen and an activated group (i.e., a phosphoramidate or H-phosphonate) on a 5'-exocyclic carbon has the structure:

(A1)

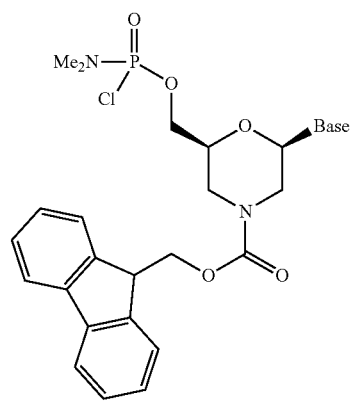

or

-continued (B1)

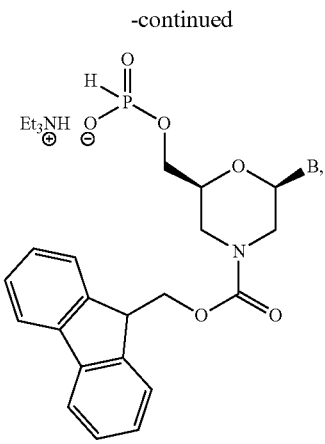

wherein:
Base or B is a nucleobase selected from guanine (Formula (IA1-IB1)), adenine (Formula (IIA1-IIB1)), cytosine (Formula (IIIA1-IIIB1)), and thymine (Formula (IVA1-IVB1)).

In embodiments, the present disclosure provides a method of preparing a phosphoramidate morpholino oligomer (PMO), the method comprising: coupling a solid support, morpholino subunit monomer or an oligomer thereof, with a monomer of Formula (I) having the structure:

(I)

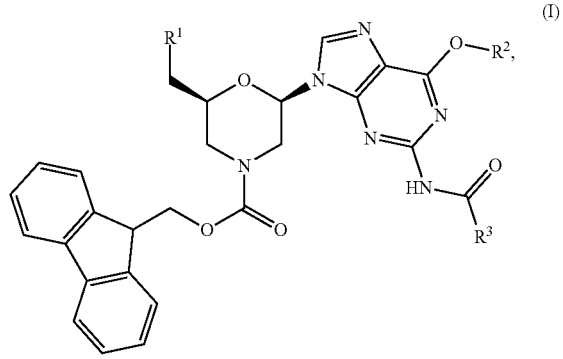

wherein:
R¹ is a protected or unprotected hydroxyl group, a chlorophosphoramidate group, a phosphoramidate linkage to the morpholino ring nitrogen of a morpholino subunit monomer, a phosphoramidate linkage to the morpholino ring nitrogen of a morpholino subunit in a morpholino oligomer, or a linkage to a solid support;
R² is a protecting group (e.g., alkyl or alkylenearyl, each of which is optionally substituted); and R³ is a protecting group (e.g., alkyl, alkylenearyl (e.g., —CH₂Ph), or alkylenearyloxy (e.g., —CH₂OPh), each of which is optionally substituted).

In embodiments, the present disclosure provides a method of preparing a phosphoramidate morpholino oligomer (PMO) comprising:

(a) loading an Fmoc-protected morpholino monomer (i.e., monomer G, A, C, or T) onto a resin, thereby producing a solid-supported monomer (see Formulas (IA-IF), (IIA-IIF), (IIIA-IIIF), and (IVA-IVF));

(b) deprotecting the Fmoc group on the solid-supported morpholino monomer of step (a) by treatment with a solution of 10% piperidine in DMF (deprotection solution);

(c) coupling the free amine of the solid-supported morpholino monomer of step (b) with a Fmoc-protected chlorophosphoramidate morpholino monomer (e.g., G, A, C, or T) provided in a solution comprising lithium bromide (LiBr) and diisopropylethylamine (DIPEA) (coupling solution), thereby producing a dimer;

(d) capping the unreacted solid-supported morpholino monomer remaining after the coupling of step (c) by treating the mixture with a 1:1 solution of 10% benzoic anhydride in NMP and 10% DIPEA in NMP (capping solution);

(e) repeating the Fmoc-deprotection, coupling, and capping cycle for each Fmoc-protected monomer added, thereby producing a PMO; and (f) cleaving the PMO from solid support by treating dried resin-loaded PMO with a solution of trifluoroacetic acid (TFA) in DCM, wherein at least one Fmoc-protected morpholino monomer of step (a) or (c) is a G-monomer of Formula (I).

In embodiments, the G-monomer of Formula (I) has the structure:

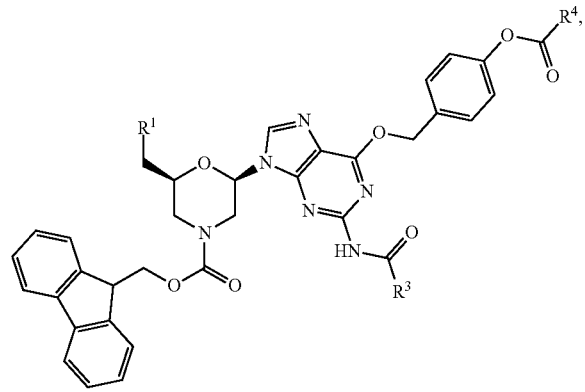

wherein R¹, R³, and R⁴ are as defined above.

In embodiments, the loading of step (a) comprises swelling 2-chlorotrityl chloride (CTC) resin in NMP for about 30 minutes. In embodiments, the monomer of step (a) is allowed to react with the resin (e.g., CTC resin) for about 1 h to about 15 h, including about 1 h, about 2 h, about 3 h, about 4 h, about 5 h, about 6 h, about 7 h, about 8 h, about 9 h, about 10 h, about 11 h, about 12 h, about 13 h, about 14 h, about 15 h, or any range or value therebetween.

In embodiments, the deprotection solution is added until the solid-supported monomer is covered. In embodiments, the deprotection is carried out for a period of about 5 minutes, about 10 minutes, about 15 minutes, about 20 minutes, about 25 minutes, or about 30 minutes. In embodiments, the deprotection solution is drained after the reaction period and a second portion of deprotection solution is added. In embodiments, the second deprotection solution is allowed to react for a period of about 5 minutes.

In embodiments, the coupling of step (c) is carried out at room temperature. In embodiments, the coupling of step (c) is carried out at elevated temperature. As used herein "elevated temperature" refers to a temperature that is above room temperature. Generally, room temperature is approximately 20° C. or 68° F. In embodiments, the elevated temperature ranges from about 25° C. to about 100° C. (e.g., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., or about 100° C.). In embodiments, the elevated temperature is about 90° C. In embodiments, the coupling solution comprises about 1-5 eq of monomer in DMI, about 1-5 eq of LiBr in DMI, and about 0.5-10 eq of DIPEA in DMI. In embodiments, the coupling solution comprises 2 eq of monomer, 2 eq of LiBr and 1 eq of DIPEA. In embodiments, the solid-supported monomer and coupling solution are reacted for about 5 minutes, about 10 minutes, about 15 minutes, about 20 minutes, about 25 minutes, or about 30 minutes. In embodiments, the solid-supported monomer and coupling solution are reacted for about 5 minutes.

In embodiments, the capping solution of step (d) is allowed to react with unreacted solid-supported monomer for about 5 to 15 minutes at room temperature. In embodiments, the capping solution of step (d) is allowed to react with unreacted solid-supported monomer for about 5 minutes at room temperature. In embodiments, the capping solution comprises a 1:1 mixture (v/v) of 10% benzoic anhydride in NMP and 10% DIPEA in NMP.

In the embodiments, the PMO has the structure of Formula (V):

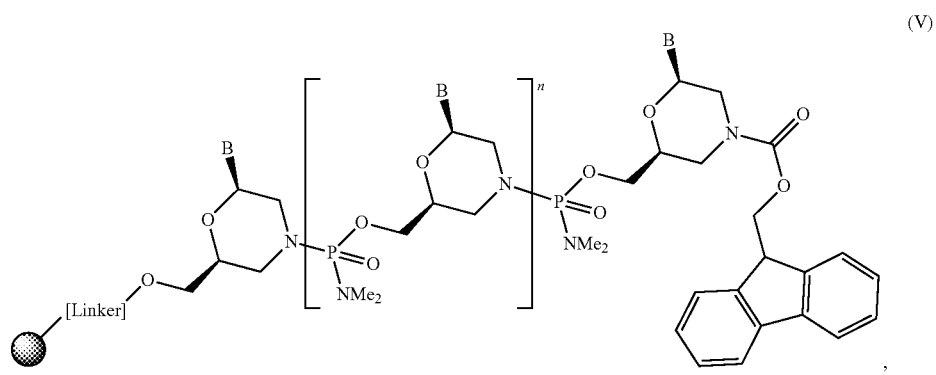

wherein:

each B is a nucleobase independently selected from adenine, cytosine, guanine and thymine, wherein at least one B is guanine;

"Linker" is a functional handle covalently attaching a morpholino subunit monomer to a solid support, which comprises of either trityl (e.g., 2-chlorotrityl), aminomethyl, p-alkoxybenzyl alcohol, 4-(4-hydroxymethyl-3-methoxyphenoxy)butyric acid, 4-[(2,4-dimethoxyphenyl)(amino)methyl]phenoxyacetic acid, or (RS)-2-{[5-(Fmoc-amino)dibenzo[a,d]cycloheptane-2-yl]oxy}acetic acid, each of which is optionally functionalized with a succinic acid; and n is 0 to 30.

In embodiments, n is 0 to 15. In embodiments, n is 0 to 10. In embodiments, n is 0 to 5. In embodiments, n is 1 to 30. In embodiments, n is 1 to 15. In embodiments, n is 1 to 10. In embodiments, n is 1 to 5.

In embodiments, the coupling reaction between a solid-supported morpholino monomer and an Fmoc-protected morpholino monomer comprising an activated phosphoramidate group includes treatment with a solution comprising lithium bromide (LiBr) and diisopropylethylamine (DIPEA). In embodiments, the coupling reaction is carried out at room temperature, e.g., about 20° C. In embodiments, the coupling reaction is carried out at a temperature from about 50° C. to about 100° C., including about 50° C., about 55° C., about 60° C., about 65° C., about 70° C., about 75° C., about 80° C., about 85° C., about 90° C., about 95° C., or about 100° C., and all ranges and values therebetween. In embodiments, the coupling reaction is carried out at about 90° C.

As described herein, Applicant surprising found that bis-protecting the guanine of a Fmoc morpholino monomer results in more efficient and higher yielding synthesis of PMOs. Synthesis of PMOs using guanine containing one protecting group gives rise to an undesirable byproduct. While the mechanism for the generation of this byproduct is unknown, it is often difficult to remove from the desired product during purification. Even with multiple rounds of chromatographic separation methods, it is difficult to completely remove this from the desired product. Using the approach to bis-protect guanine resolves this issue, thus increasing the efficiency and yield of PMO synthesis.

Furthermore, without being bound by any particular theory, the use of Fmoc in place of trityl on a morpholino improves the efficiency of PMO synthesis by reducing reaction times, particular the coupling reaction mediated by LiBr. The purity of the final PMO product is also improved when Fmoc-protection is relied on. This is because the acid deprotection required to remove trityl and related groups (e.g., monomethoxytrityl and dimethoxytrityl) can be replaced with mild basic conditions. Since PMOs can decompose if subjected to acid for prolonged times, deprotection under basic conditions alleviates this problem, and therefore provides higher purity PMO products. An added benefit is that Fmoc deprotections are completed quickly and do not require subsequent neutralization steps. As a result, the overall cycle times for installation of each morpholino monomer is reduced significantly.

INCORPORATION BY REFERENCE

The contents of all documents cited herein are hereby incorporated herein by reference in their entirety.

Examples

Figure 1:
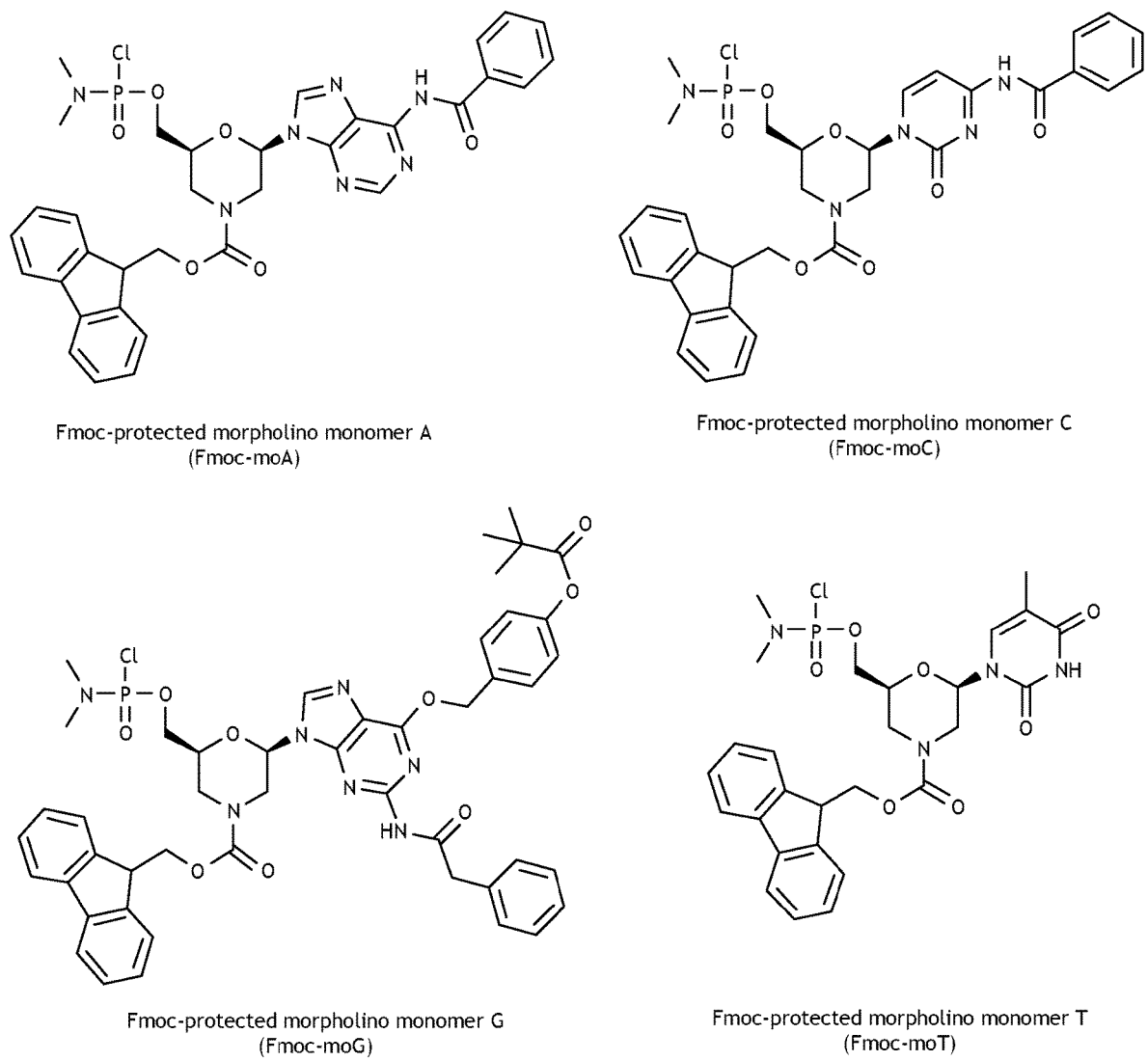
FIG. 1 shows non-limiting examples of activated morpholino monomers of the present disclosure.
Figure 2A:
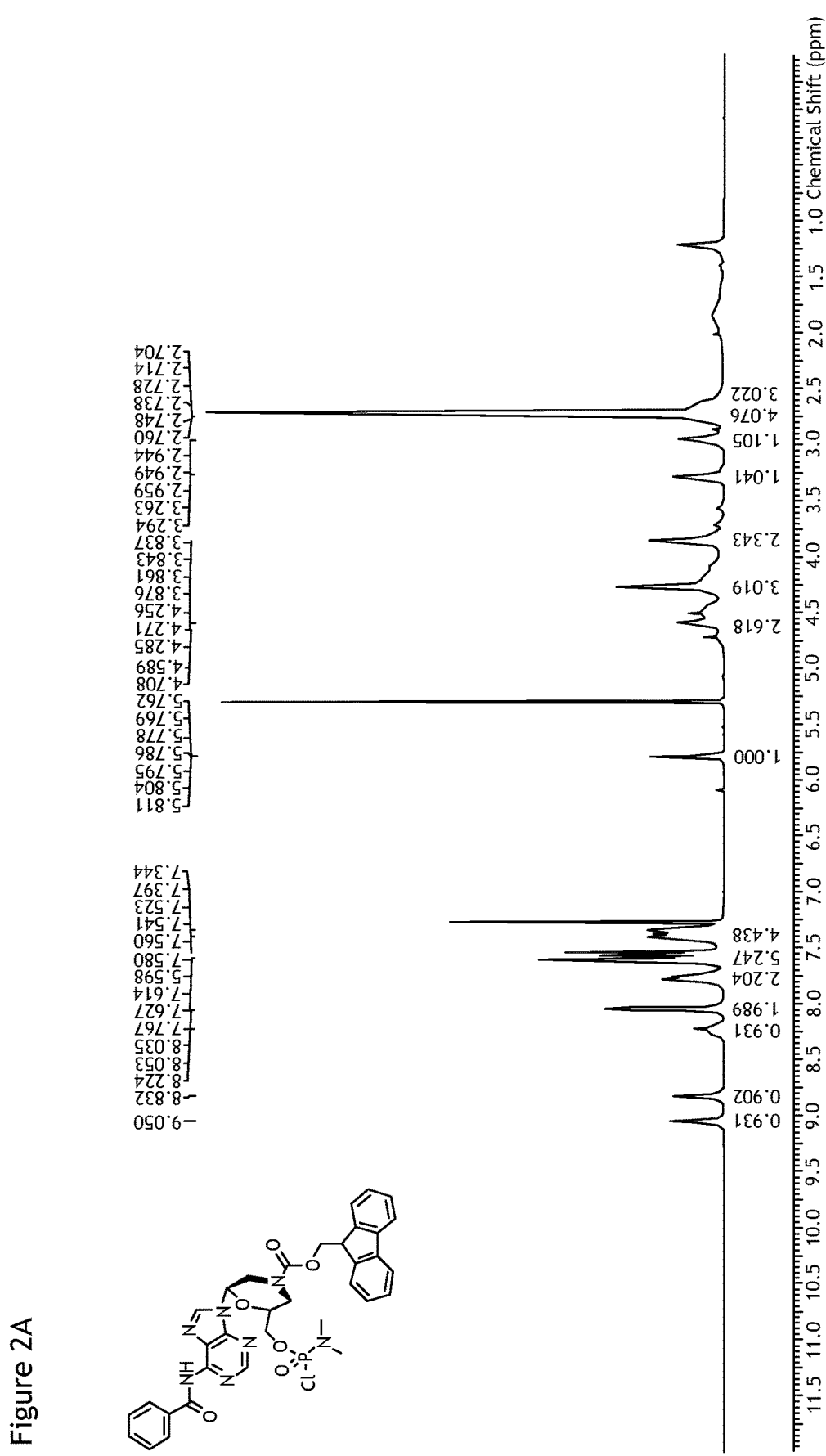
FIG. 2A shows the $^1$H NMR (400 MHz, CDCl3) of Fmoc Monomer A.
Figure 2B:
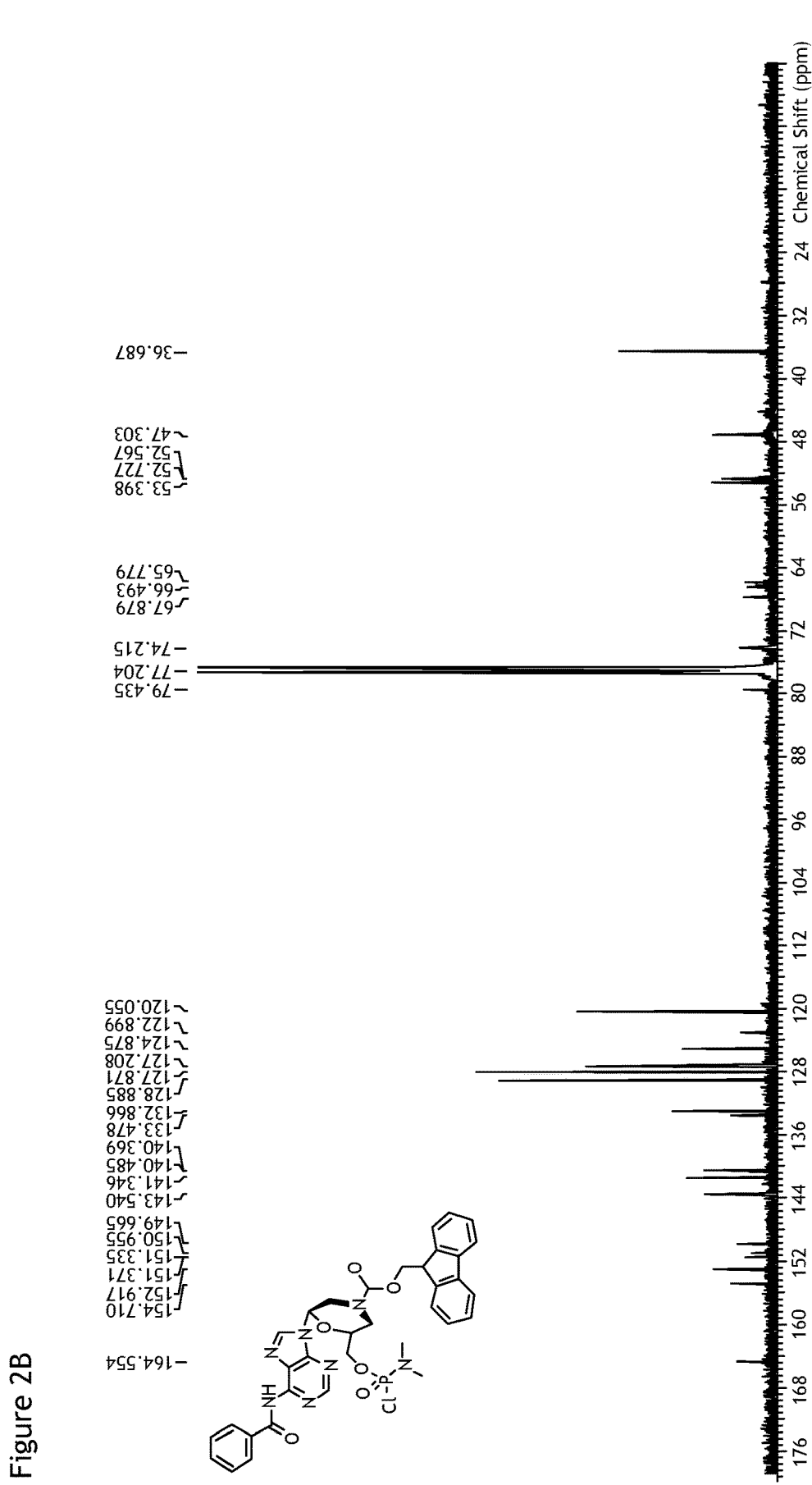
FIG. 2B shows the $^{13}$C NMR (CDCl3) of Fmoc Monomer A.
Figure 2C:
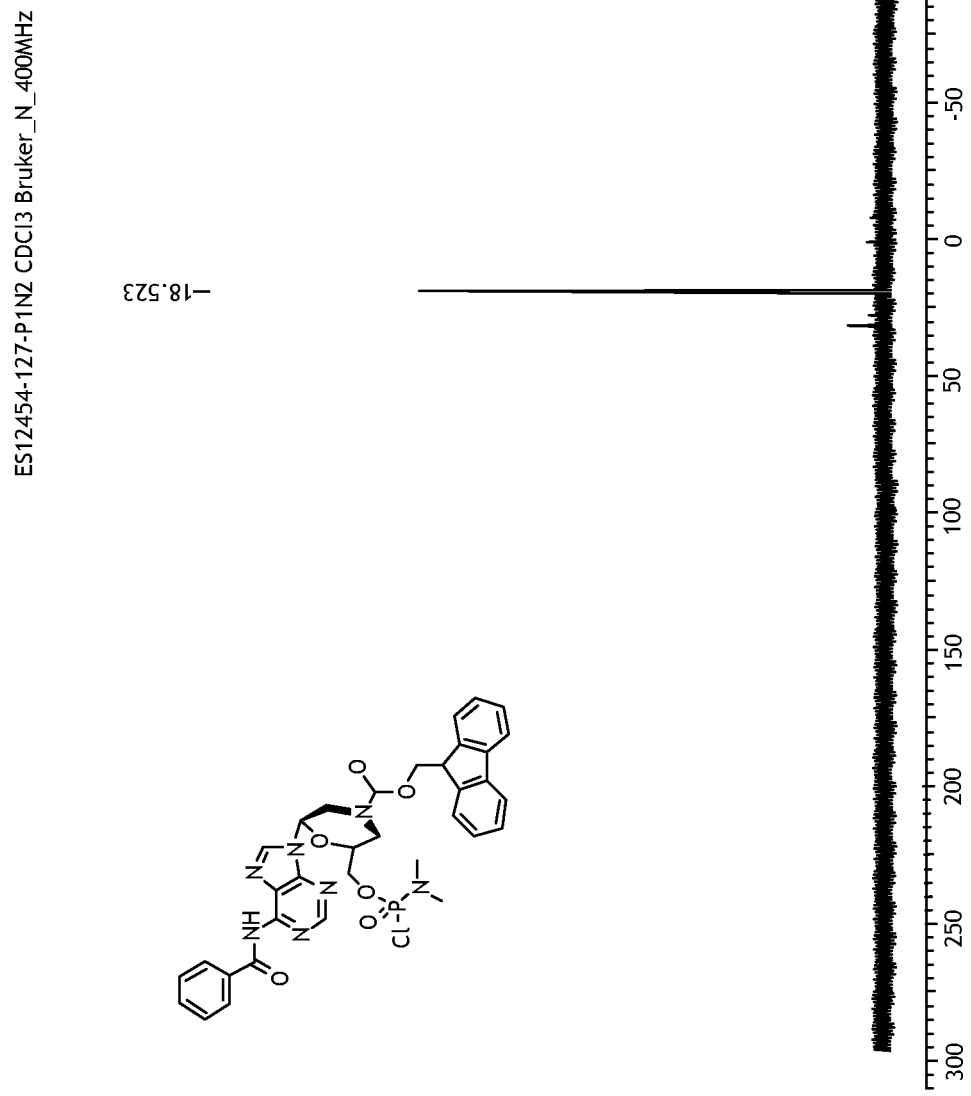
FIG. 2C shows the $^{31}$P NMR (CDCl3) of Fmoc Monomer A.
Figure 2D:
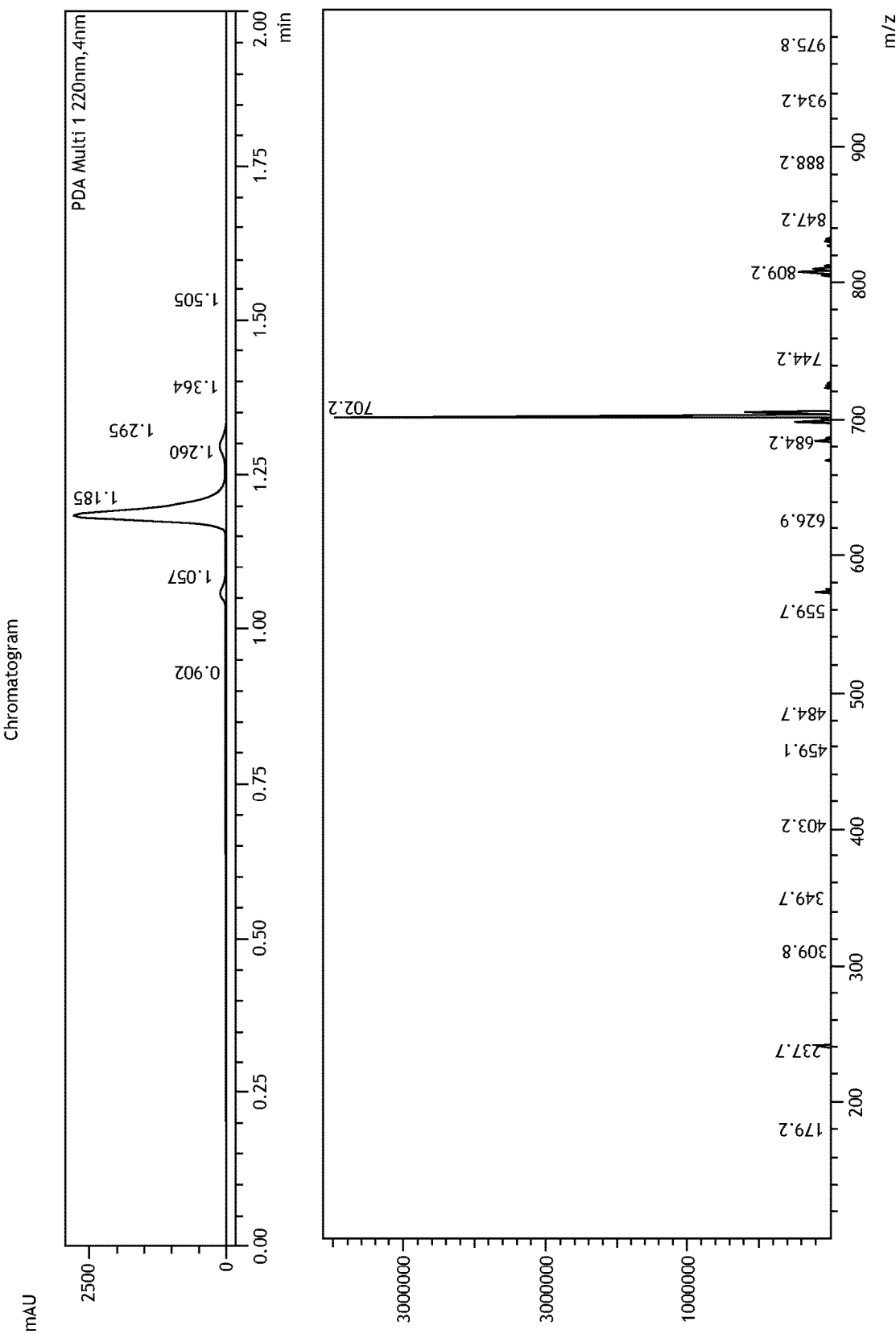
FIG. 2D shows the LCMS chromatogram of Fmoc Monomer A (calculated molecular weight=702.10).

The Fmoc monomers of FIG. 1 were prepared as described below.

Example 1. Synthesis of Fmoc Morpholino Monomer A

A-2 was prepared via an oxidative cleavage/reductive amination sequence, which after Fmoc protection, produced A-3. Treatment with N,N-dimethylphosphamidodichlorate in the presence of LiBr and NEM provided morpholino monomer A.

Scheme 1

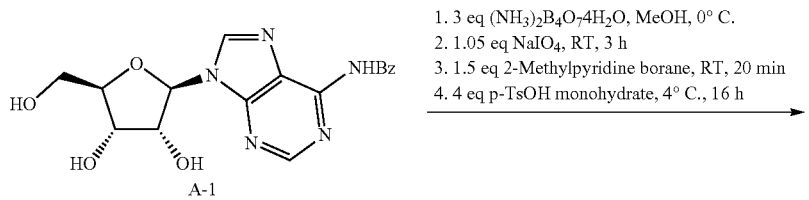

1. 3 eq (NH$_3$)$_2$B$_4$O$_7$·4H$_2$O, MeOH, 0° C.
2. 1.05 eq NaIO$_4$, RT, 3 h
3. 1.5 eq 2-Methylpyridine borane, RT, 20 min
4. 4 eq p-TsOH monohydrate, 4° C., 16 h

A-1

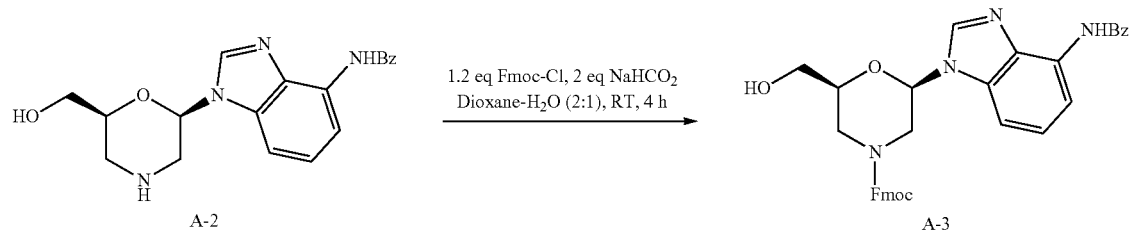

1.2 eq Fmoc-Cl, 2 eq NaHCO$_2$
Dioxane-H$_2$O (2:1), RT, 4 h

A-2          A-3

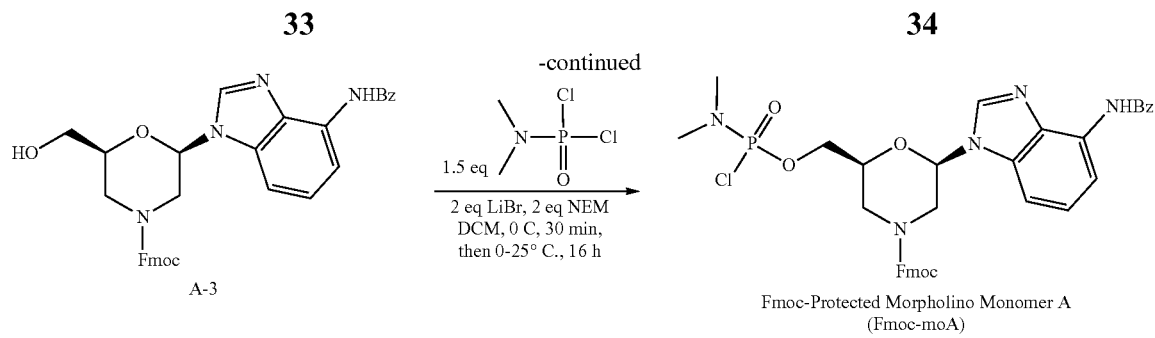

Fmoc-Protected Morpholino Monomer A
(Fmoc-moA)

The structure of Fmoc-moA was confirmed by the characterization data provided in FIGS. 2A-2D.

Example 2. Synthesis of Fmoc Morpholino Monomer C

C-2 was prepared via an oxidative cleavage/reductive amination sequence, which after Fmoc protection, produced C-3. Treatment with N,N-dimethylphosphamidodichlorate in the presence of LiBr and NEM provided morpholino monomer C.

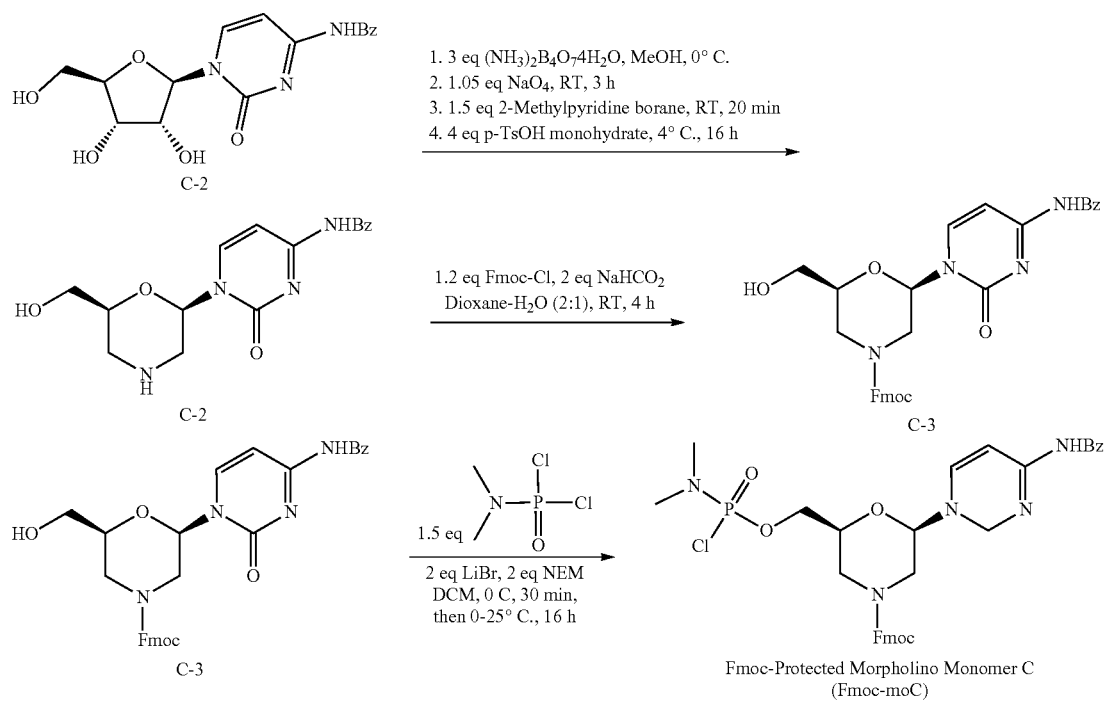

Scheme 2

Fmoc-Protected Morpholino Monomer C
(Fmoc-moC)

The structure of Fmoc-moC was confirmed by the characterization data provided in FIGS. 3A-3D.

Example 3. Synthesis of Fmoc Morpholino Monomer T

T-2 was prepared via an oxidative cleavage/reductive amination sequence, which after Fmoc protection, produced T-3. Treatment with N,N-dimethylphosphamidodichlorate in the presence of LiBr and NEM provided morpholino monomer T.

Scheme 3

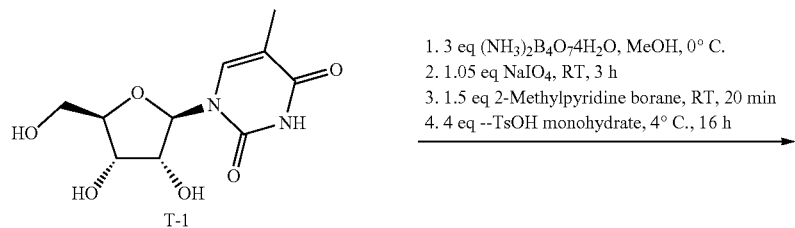

The structure of Fmoc-moT was confirmed by the characterization data provided in FIGS. 4A-4D.

Example 4. Synthesis of Fmoc Morpholino Monomer G

Scheme 4 describes the synthesis of di-protected Fmoc morpholino monomer G starting from commercially available guanosine. G-1 was prepared as described in detail in U.S. Pat. Nos. 5,185,444 and 8,969,551. G-2 was prepared as described in U.S. Pat. No. 7,943,762. G-3, G-4, G-5, G-6, and G-7 were prepared as described in detail in U.S. Pat. No. 8,969,551. To install the Fmoc protecting group, trityl was removed from G-7 using 3% trifluoroacetic acid (TFA) in a 1:1 mixture of DCM/MeOH. The deprotected compound was subjected to Fmoc-C$_1$ (1.2 eq) and NaHCO3(2 eq) in dioxane-water (see Ghosh, U. et al. "Synthesis of Phosphoramidate Morpholino Oligonucleotides Using Trityl and Fmoc Chemistry-A New Method Amendable to Automated Synthesizer" ChemRxiv, posted Jun. 8, 2020) to provide G-8, which was then treated with N,N-dimethylphosphamidodichlorate (see Bhadra, J. et al. "Synthesis of Morpholino Monomers, Chlorophosphoramidate Monomers, and Solid-Phase Synthesis of Short Morpholino Oligomers" Curr. Prot. in Nucleic Acid Chem. 2015, 62, p. 4.65.1-4.65.26) in the presence of LiBr (2 eq) and NEM (2 eq) to provide morpholino monomer G (G-9).

Scheme 4

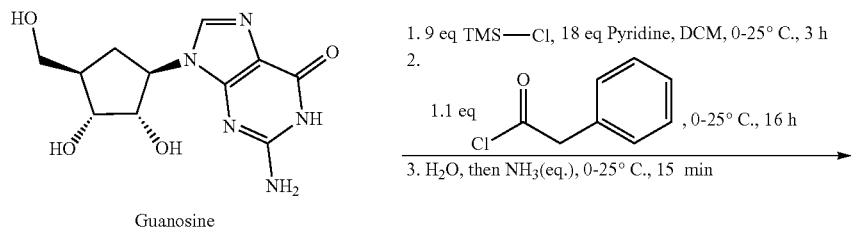

-continued
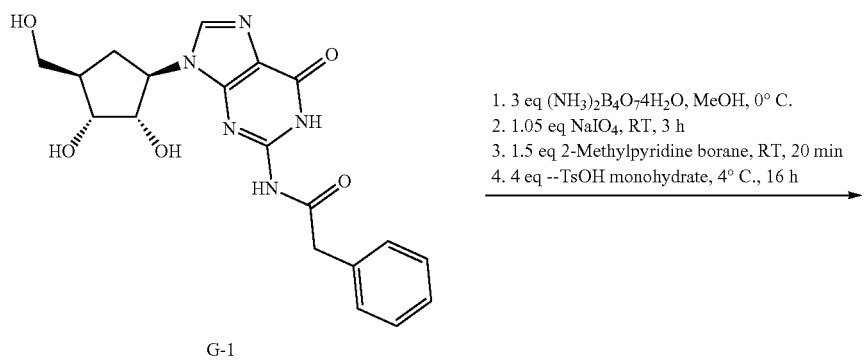
G-1
1. 3 eq (NH$_3$)$_2$B$_4$O$_7$4H$_2$O, MeOH, 0° C.
2. 1.05 eq NaIO$_4$, RT, 3 h
3. 1.5 eq 2-Methylpyridine borane, RT, 20 min
4. 4 eq --TsOH monohydrate, 4° C., 16 h
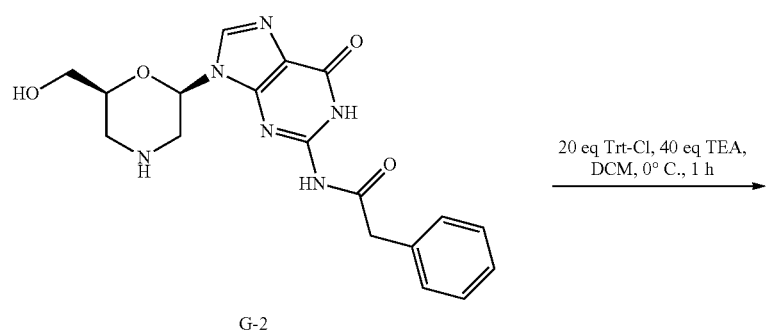
G-2
20 eq Trt-Cl, 40 eq TEA, DCM, 0° C., 1 h
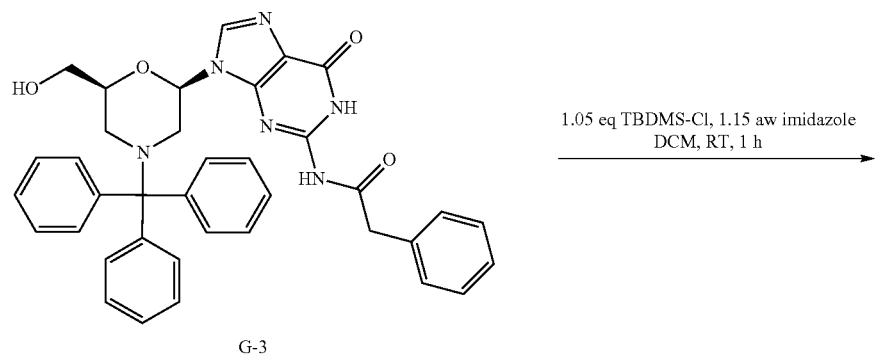
G-3
1.05 eq TBDMS-Cl, 1.15 aw imidazole DCM, RT, 1 h
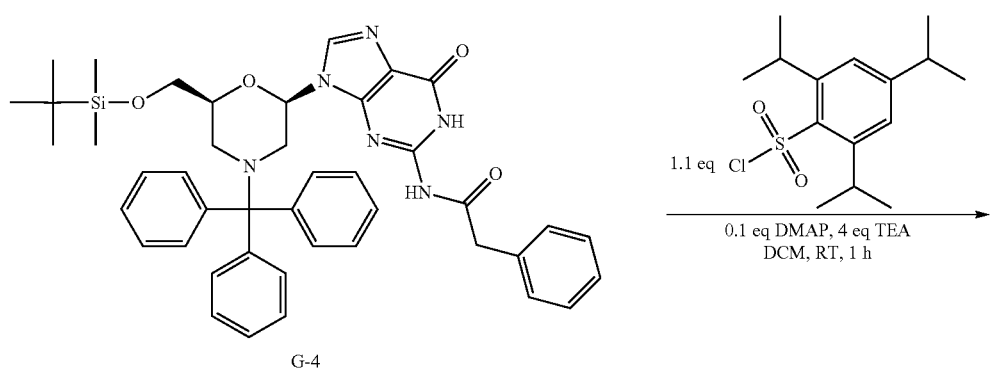
G-4
1.1 eq
0.1 eq DMAP, 4 eq TEA DCM, RT, 1 h -continued
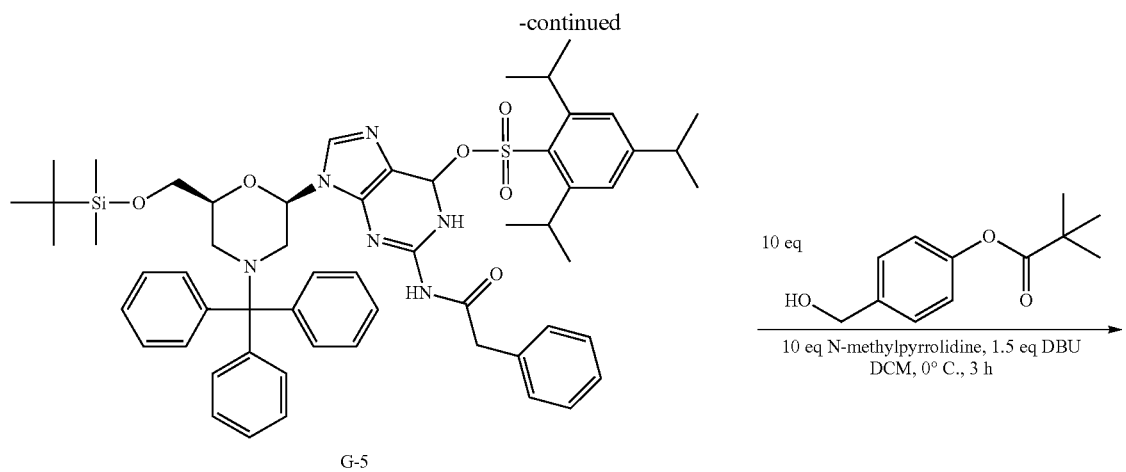
G-5
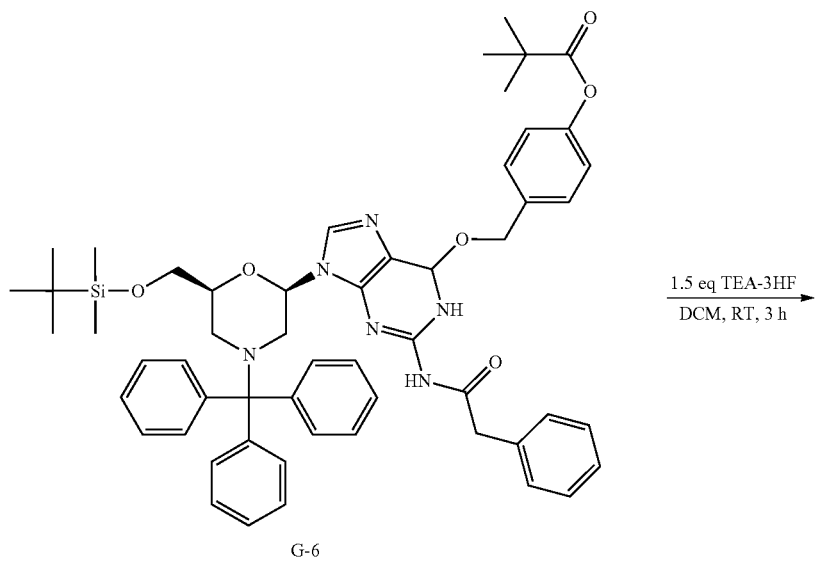
G-6
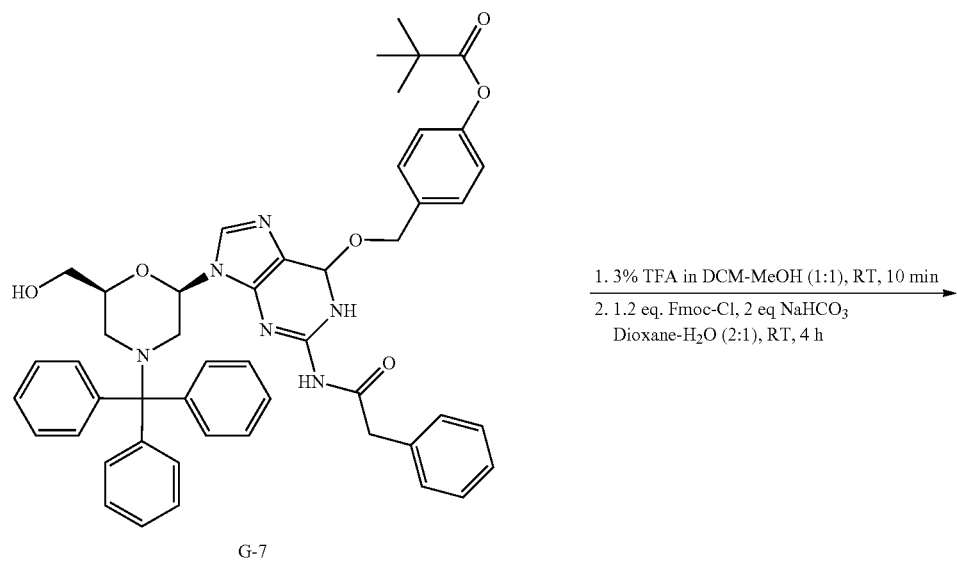
G-7

-continued
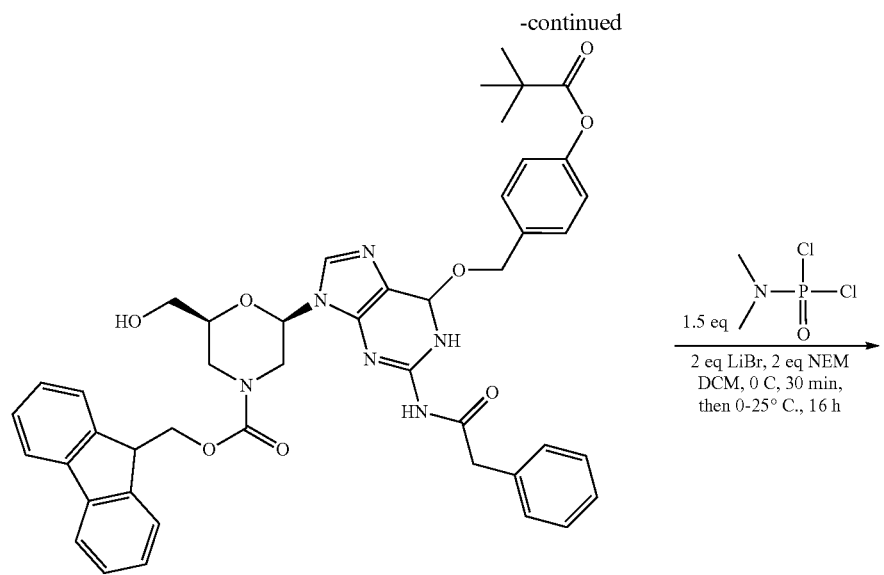
G-8
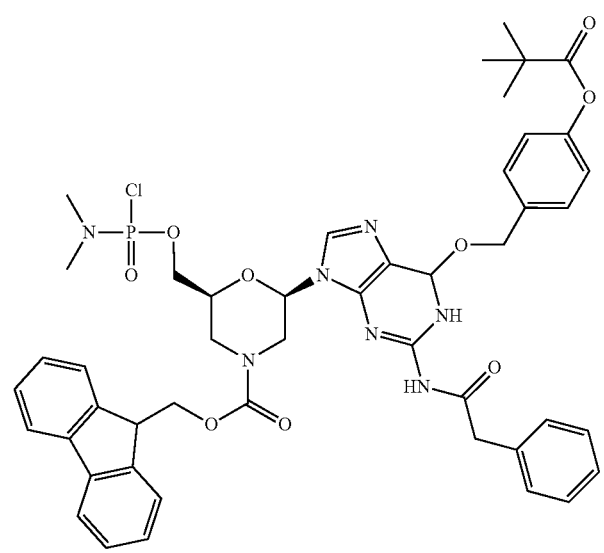
G-9
Fmoc-Protected Morpholino Monomer G
(Fmoc-moG)

The structure of Fmoc-moG was confirmed by the characterization data provided in FIGS. 5A and 5B.

Example 5. Room Temperature Protocol for the Synthesis of PMOs with Monomers Containing 3'-Fmoc Protecting Groups

SEQ ID NO: 1

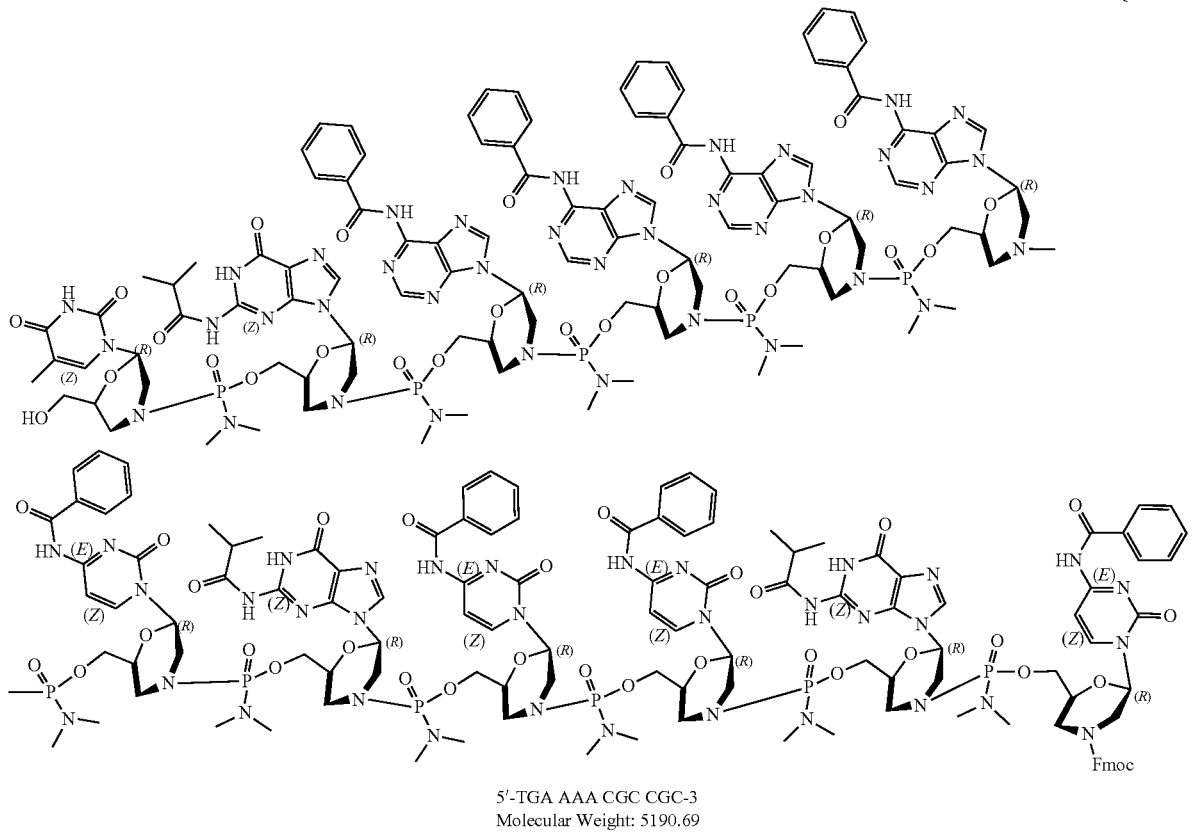

5'-TGA AAA CGC CGC-3
Molecular Weight: 5190.69

Synthesis was performed in a peptide synthesis vessel at room temperature. Karl Fischer analysis of solvents was performed before beginning synthesis (water content ≤100 ppm).

Resin Loading (Scheme 5):

2-chlorotrityl chloride resin was swelled in NMP for 30 minutes. A resin loading solution was prepared containing 1.5-2 equivalents of 5'-OH-Fmoc morpholino monomer and 3-4 equivalents of DIPEA dissolved in anhydrous DCM. The resin loading solution was added to the CTC resin and the mixture was stirred overnight at room temperature. The resin was then capped by treating it with a solution of 17:2:1 dichloromethane/methanol/DIPEA three times for 30 minutes each at room temperature. Resin was then washed with DMF 3 times and DCM 3 times before beginning PMO synthesis protocol. Resin loading was checked by Fmoc deprotection and UV analysis of dibenzofulvene-piperidine adduct.

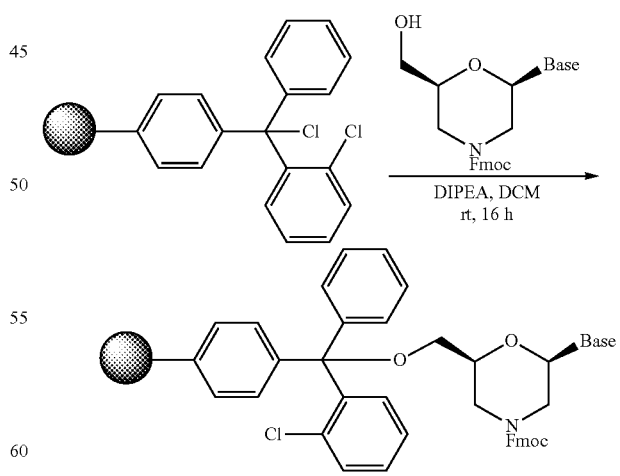

Scheme 5. Loading of CTC Resin with 5'-OH-Fmoc Morpholino Monomer.

Synthesis of PMOs—room temperature protocol:
1. Deprotection Solution (10% piperidine dissolved in DMF) was added to resin until it is covered with solution and the mixture was reacted for 5 minutes. The solution was drained from resin and another portion of Deprotection Solution was added. After reacting for 5 minutes, the solution was drained from the resin.
2. The resin was washed three times with DMF, followed by anhydrous DMI three times.
3. Coupling Solution[1] was then added to resin and was vortexed for 60 min at room temperature.
4. The resin was washed three times with DMF, followed by three times with NMP.
5. The resin was capped by adding Capping Solution (1:1 solution of 10% benzoic anhydride in NMP and 10% diisopropylethylamine in NMP) to resin and allowed to react for 5 minutes at room temperature.
6. The resin was washed three times with NMP, followed by three times with DMF.
7. Steps 1 through 6 were repeated for each monomer until a full length PMO sequence has been produced.

[1]Coupling solution includes 0.2 M morpholino monomer (5 equivalents), 0.2 M LiBr (5 equivalents), and 0.4 M DIPEA (10 equivalents). This solution was prepared by first dissolving monomer and LiBr sequentially. Then, DIPEA was added and mixed immediately before adding to resin.

Cleavage Protocol:
After the last coupling cycle was performed, the resin was washed three times with methanol and then was dried under reduced pressure. To the dried resin was added 2.5% TFA dissolved in DCM and was left to react for 30 minutes at room temperature. The solution was filtered and subsequently quenched by adding it to a solution of 10% pyridine in methanol. This neutralized solution was then concentrated and redissolved in NH4OH to react at 50° C. for 16 hours.

Synthesis of 5'-TGAAAACGCCGC-3' (SEQ ID NO: 1; Molecular Weight 5190.69)

0.0125 mmol of CTC resin was calculated using the desired resin loading and was weighed into a peptide synthesis vessel. NMP was then added until the solvent completely covered the solid resin and then rested for 30 minutes to swell. After draining the solvent from resin, 0.025 mmol of 5'-OH Fmoc-moT was measured and dissolved in 0.125 mL of DCM. 0.05 mmol of DIPEA was added to this solution and mixed before adding to resin. The solution and resin were allowed to react overnight at room temperature. The solution was drained from resin and was then treated with a solution of 17:2:1 dichloromethane/methanol/DIPEA three times for 30 minutes each at room temperature to cap the unreacted sites on the CTC resin. The resin was washed 3 times with DMF before beginning the PMO synthesis protocol as described above.

Once synthesis was complete, the first step of cleavage was performed. A solution of 2.5% TFA in DCM was added to resin and was left to react for 30 minutes at room temperature. The solution was filtered, neutralized, and concentrated before performing an analysis to check the quality of synthesis.

Results: 5'-TGAAAACGCCGC-3' (SEQ ID NO: 1) was prepared as described from the above room temperature protocol. The structure of this 12-mer PMO was confirmed by the LCMS data shown in FIG. 6.

Example 6. High Temperature Protocol for the Synthesis of PMOs with Monomers Containing 3'-Fmoc Protecting Groups Resin loading was carried out according to the procedure described in Example 5.

Synthesis of PMOs—higher temperature protocol:
1. Deprotection Solution (10% piperidine dissolved in DMF) was added to resin until it is covered with solution and the mixture was reacted for 5 minutes. The solution was drained from resin and another portion of Deprotection Solution was added. After reacting for 5 minutes, the solution was drained from the resin.
2. The resin was washed three times with DMF
3. Coupling Solution[2] was then added to resin and reacted at 90° C. for 5 min. The resin was drained, and another batch of coupling solution was added to resin and reacted at 90° C. for 5 min.
4. The resin was washed three times with DMF.
5. The resin was capped by adding Capping Solution (1:1 solution of 10% benzoic anhydride in NMP and 10% diisopropylethylamine in NMP) to resin and allowed to react for 5 minutes at room temperature.
6. The resin was washed three times with DMF.
7. Steps 1 through 6 were repeated for each monomer until a full length PMO sequence has been produced.

[2]Coupling solution was preparing by:

1. Making solutions of each of the following:
   A. 2 eq of morpholino monomer (0.2 M) in DMI,
   B. 2 eq of LiBr (0.2 M) in DMI, and 0.4 M, and
   C. 1 eq of DIPEA (0.1 M) in DMI.
2. Mixing the solutions of A, B, and C together prior to coupling.

Cleavage protocol:
After the last coupling cycle was performed, the resin was washed three times with methanol and then was dried under reduced pressure. To the dried resin was added 2.5% TFA dissolved in DCM and was left to react for 30 minutes at room temperature. The solution was filtered and subsequently quenched by adding it to a solution of 10% pyridine in methanol. This neutralized solution was then concentrated and redissolved in NH$_4$OH to react at 50° C. for 16 hours.

A PMO having the sequence TGACGC was prepared using the higher temperature protocol. The steps used in the synthesis are shown in Table 1.

TABLE 1

Protocol for the synthesis of 5-mer PMO having the sequence TGACGC

| Step | Description | Time | Temperature | Mixture |
|---|---|---|---|---|
| 1 | Deprotection | 2 × 5 minutes | Room temp. | 10% Pip.inDMF |
| 2 | Wash | 3 × 30 seconds | Room temp. | DMF |
| 3 | Coupling | 2 × 5 minutes | 90° C. | Coupling Solution2 |
| 4 | Wash | 3 × 30 seconds | Room temp. | DMF |
| 5 | Capping | 1 × 5 minutes | Room temp. | Capping Solution |
| 6 | Wash | 3 × 30 seconds | Room temp. | DMF |

Results: The product prepared from the higher temperature protocol was confirmed by LCMS (FIG. 7) to be the desired PMO having the sequence TGACGC. By increasing the temperature to 90° C., the targeted product was prepared in similar quality, but 2.7-times faster than with the room temperature protocol (FIG. 8) and at least 4.7-times faster than the synthesis using trityl protected morpholino monomers.

What is claimed is:

1. A compound of Formula (I) having the structure:

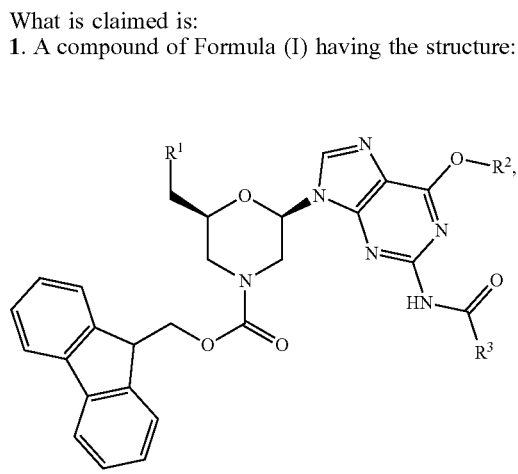

wherein:
$R^1$ is a protected or unprotected hydroxyl group, a chlorophosphoramidate group, a phosphoramidate linkage to the morpholino ring nitrogen of a morpholino subunit monomer, a phosphoramidate linkage to the morpholino ring nitrogen of a morpholino subunit in a morpholino oligomer, or a linkage to a solid support;
$R^2$ is alkyl or alkylenearyl, each of which is optionally substituted; and
$R^3$ is alkyl, alkylenearyl, or alkylenearyloxy, each of which is optionally substituted.

2. The compound of claim 1, wherein $R^1$ is —OH, —OP(=O)(Cl)N(CH$_3$)$_2$, or a linkage to a solid support.

3. The compound of claim 2, wherein the linkage to a solid support comprises trityl, aminomethyl, p-alkoxybenzyl alcohol, 4-(4-hydroxymethyl-3-methoxyphenoxy)butyric acid, 4-[(2,4-dimethoxyphenyl)(amino)methyl]phenoxyacetic acid, or (RS)-2-{[5-(Fmoc-amino)dibenzo[a,d]cycloheptane-2-yl]oxy}acetic acid, each of which is optionally functionalized with a terminal succinic acid.

4. The compound of claim 1, wherein $R^2$ is substituted alkylenearyl of formula

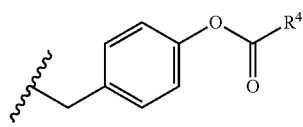

wherein $R^4$ is alkyl, aryl, or —CH$_2$aryl.

5. The compound of claim 4, wherein $R^4$ is t-butyl, phenyl, or benzyl.

6. The compound of claim 1, wherein $R^3$ is —CH$_2$Ph or —CH(CH$_3$)$_2$.

7. A method of preparing a phosphoramidate morpholino oligomer (PMO), the method comprising:
coupling a solid support, morpholino subunit monomer or an oligomer thereof, with a monomer of Formula (I) having the structure:

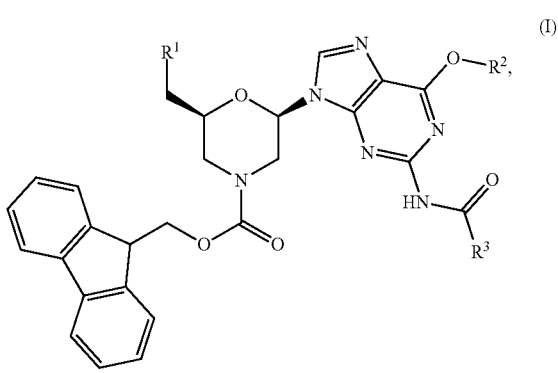

wherein:
$R^1$ is a protected or unprotected hydroxyl group, a chlorophosphoramidate group, a phosphoramidate linkage to the morpholino ring nitrogen of a morpholino subunit monomer, a phosphoramidate linkage to the morpholino ring nitrogen of a morpholino subunit in a morpholino oligomer, or a linkage to a solid support;
$R^2$ is alkyl or alkylenearyl, each of which is optionally substituted; and
$R^3$ is alkyl, alkylenearyl, or alkylenearyloxy, each of which is optionally substituted.

8. The method of claim 7, wherein the method comprises:
(a) coupling a solid-supported morpholino monomer comprising an unprotected ring nitrogen with a first morpholino subunit monomer comprising a fluorenylmethyoxycarbonyl (Fmoc)-protected morpholino ring nitrogen and an activated phosphoramidate group on a 5'-exocyclic carbon, thereby forming a first phosphorodiamidate linkage between the 5'-exocyclic carbon of the first morpholino subunit monomer and the unprotected morpholino ring nitrogen of the solid-supported morpholino subunit monomer;
(b) deprotecting the Fmoc-protected morpholino ring nitrogen to form a product comprising an unprotected morpholino ring nitrogen;
(c) optionally coupling the product from step (b) with a second morpholino subunit monomer comprising an Fmoc-protected morpholino ring nitrogen and an activated phosphoramidate group on a 5'-exocyclic carbon, thereby forming a second phosphorodiamidate linkage between the 5'-exocyclic carbon of the second morpholino subunit monomer and the unprotected morpholino ring nitrogen of the product from step (b); and (d) optionally repeating steps (b) and (c) one or more times;

wherein at least one of the first morpholino subunit monomer, the second morpholino subunit monomer, a further morpholino subunit monomer, or the solid-phase-supported morpholino subunit monomer is a protected guanine morpholino compound having the structure of Formula (I):

10. The method of claim 8, wherein

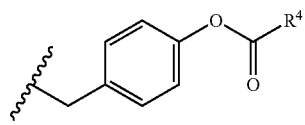

$R^4$ is alkyl, aryl, or —CH$_2$aryl.

11. The method of claim 7, wherein the compound of Formula (I) is:

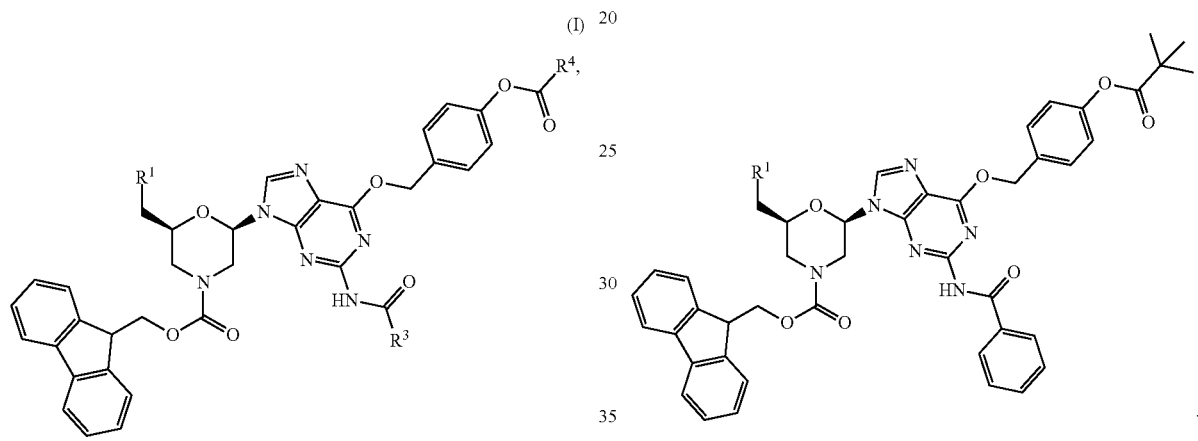

wherein:

$R^1$ is a protected or unprotected hydroxyl group, a chlorophosphoramidate group, a phosphoramidate linkage to the morpholino ring nitrogen of a morpholino subunit monomer, a phosphoramidate linkage to the morpholino ring nitrogen of a morpholino subunit in a morpholino oligomer, or a linkage to a solid support;

$R^3$ is alkyl, alkylenearyl, or alkylenearyloxy, each of which is optionally substituted; and $R^4$ is alkyl, aryl, —CH$_2$aryl or —N(C$_{1-5}$alkyl)$_2$.

9. The method of claim 7, wherein $R^1$ is —OH, —OP(=O)(Cl)N(CH$_3$)$_2$, or a linkage to a solid support, $R^2$ is 4-nitrophenethyl or

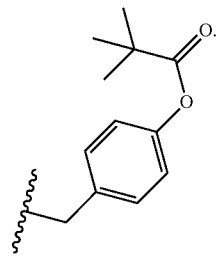 [SMILES: *Cc1ccc(OC(=O)C(C)(C)C)cc1]

12. The method of claim 7, wherein the morpholino subunit monomer comprises an Fmoc-protected morpholino ring nitrogen and an activated phosphoramidate group on a 5'-exocyclic carbon and has the structure:

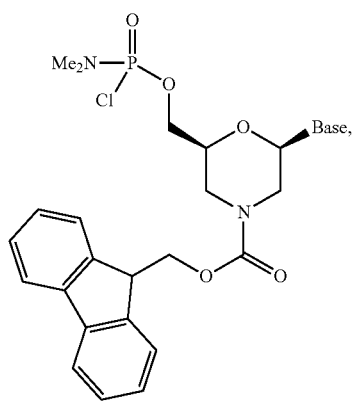

wherein:

Base is a nucleobase selected from the group consisting of guanine, adenine, cytosine, and thymine.

13. The method of claim 7, wherein the PMO has the structure of Formula (V):

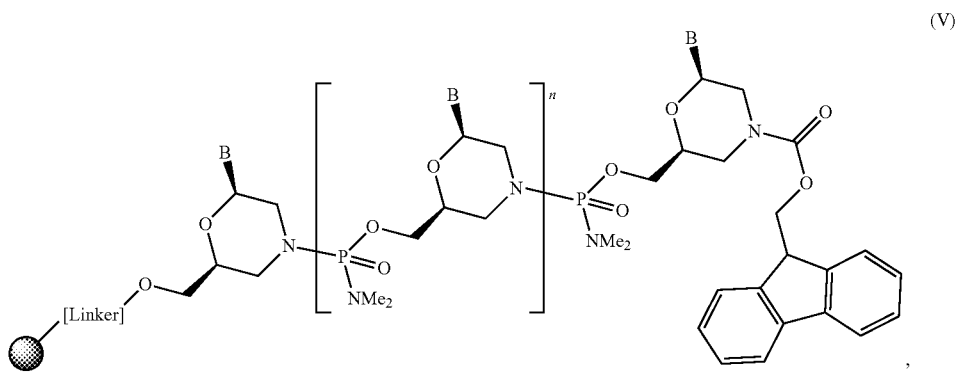

wherein:
B is a nucleobase selected from the group consisting of adenine, cytosine, guanine and thymine, wherein at least one B is guanine;
"Linker" is a functional handle covalently attaching a morpholino subunit monomer to a solid support, which comprises of either trityl, aminomethyl, p-alkoxybenzyl alcohol, 4-(4-hydroxymethyl-3-methoxyphenoxy) butyric acid, 4-[(2,4-dimethoxyphenyl)(amino)methyl] phenoxyacetic acid, or (RS)-2-{[5-(Fmoc-amino) dibenzo[a,d]cycloheptane-2-yl]oxy}acetic acid, each of which is optionally functionalized with a succinic acid; and
n is 0 to 30.

14. The compound of claim 2, wherein $R^3$ is —CH$_2$Ph or —CH(CH$_3$)$_2$.

15. The compound of claim 3, wherein $R^3$ is —CH$_2$Ph or —CH(CH$_3$)$_2$.

16. The compound of claim 1, wherein $R^2$ is 4-nitrophenethyl or

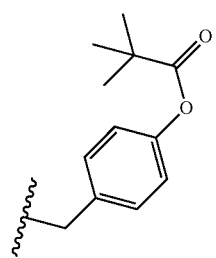

17. The compound of claim 2, wherein $R^2$ is 4-nitrophenethyl or

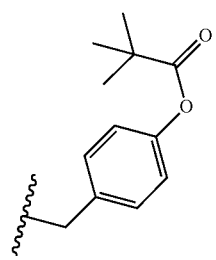

18. The compound of claim 16, wherein $R^3$ is —CH(CH$_3$)$_2$.

19. The compound of claim 17, wherein $R^3$ is —CH(CH$_3$)$_2$.

20. The compound of claim 1, wherein the compound is

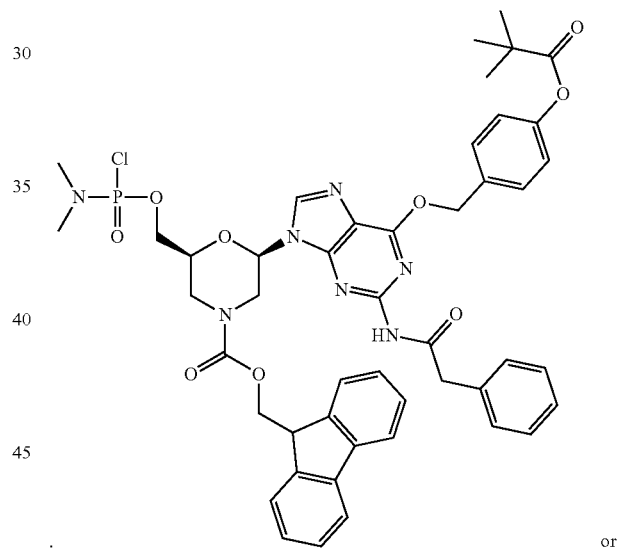

or

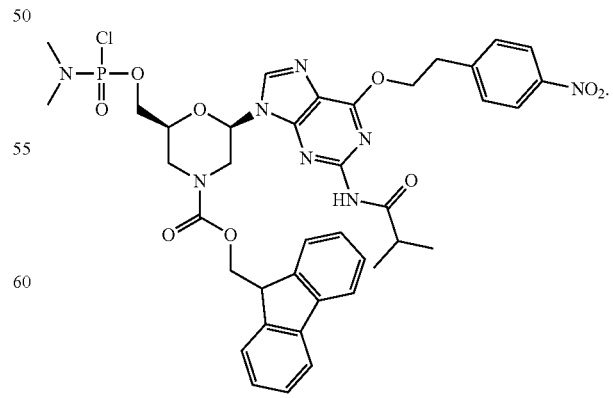

* * * * *